United States Patent
Lim et al.

(10) Patent No.: US 9,368,727 B2
(45) Date of Patent: Jun. 14, 2016

(54) ORGANIC PHOTOELECTRIC DEVICE AND IMAGE SENSOR INCLUDING THE SAME

(71) Applicant: Samsung Electronics Co., Ltd., Suwon-Si, Gyeonggi-Do (KR)

(72) Inventors: Seon Jeong Lim, Yongin-si (KR); Dong Seok Leem, Hwaseong-si (KR); Kyu Sik Kim, Jeonju-si (KR); Kyung Bae Park, Hwaseong-si (KR); Kwang Hee Lee, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/856,712

(22) Filed: Apr. 4, 2013

(65) Prior Publication Data

US 2014/0117321 A1     May 1, 2014

(30) Foreign Application Priority Data

Oct. 25, 2012  (KR) .................. 10-2012-0119252

(51) Int. Cl.
| | |
|---|---|
| *H01L 51/56* | (2006.01) |
| *H01L 51/00* | (2006.01) |
| *C07D 471/06* | (2006.01) |
| *C07C 13/62* | (2006.01) |
| *H01L 51/42* | (2006.01) |

(52) U.S. Cl.
CPC ............. *H01L 51/0056* (2013.01); *C07C 13/62* (2013.01); *C07D 471/06* (2013.01); *H01L 51/0053* (2013.01); *C07C 2103/54* (2013.01); *H01L 51/4253* (2013.01); *H01L 2251/308* (2013.01)

(58) Field of Classification Search
USPC ........................................... 136/263
See application file for complete search history.

(56) References Cited

U.S. PATENT DOCUMENTS

| | | |
|---|---|---|
| 2008/0287678 A1 | 11/2008 | Konemann |
| 2011/0020979 A1 | 1/2011 | Forrest et al. |
| 2011/0168248 A1* | 7/2011 | Koenemann et al. ......... 136/255 |
| 2011/0297234 A1 | 12/2011 | Forrest et al. |
| 2012/0138125 A1 | 6/2012 | Hammermann et al. |

(Continued)

FOREIGN PATENT DOCUMENTS

| | | |
|---|---|---|
| KR | 2008-0032231 A | 4/2008 |
| KR | 2013-0022894 A | 3/2013 |

(Continued)

OTHER PUBLICATIONS

Al-Kaysi et al. The photophysical properties of chromophores ar high (100 mM and above) concentrations in polymers and as neat solids. Physical Chemistry Chemical Physics 2006, vol. 8, p. 3453-3459.*

(Continued)

*Primary Examiner* — Jeffrey T Barton
*Assistant Examiner* — Daniel Malley, Jr.
(74) *Attorney, Agent, or Firm* — Harness, Dickey & Pierce, P.L.C.

(57) ABSTRACT

An organic photoelectric device may include an anode and a cathode facing each other and the active layer between the anode and cathode, wherein the active layer includes a compound represented by Chemical Formula 1 and a compound represented by Chemical Formula 2. Chemical Formula 1 and Chemical Formula 2 are the same as in the detailed description.

22 Claims, 32 Drawing Sheets

(56) References Cited

U.S. PATENT DOCUMENTS

| | | | |
|---|---|---|---|
| 2012/0152303 A1* | 6/2012 | Meiss et al. | 136/244 |
| 2013/0048958 A1 | 2/2013 | Lim et al. | |
| 2013/0062595 A1 | 3/2013 | Park et al. | |
| 2013/0105768 A1 | 5/2013 | Leem et al. | |
| 2013/0112947 A1 | 5/2013 | Lee et al. | |
| 2013/0174910 A1* | 7/2013 | Yasukawa et al. | 136/263 |
| 2014/0008619 A1 | 1/2014 | Lee et al. | |

FOREIGN PATENT DOCUMENTS

| | | |
|---|---|---|
| KR | 2013-0028488 A | 3/2013 |
| KR | 2013-0047367 A | 5/2013 |
| KR | 20130050082 A | 5/2013 |
| KR | 2013-0082289 A | 7/2013 |
| KR | 2014-0006597 A | 1/2014 |
| WO | WO-2010/133205 A1 | 11/2010 |
| WO | WO-2010/139310 A2 | 12/2010 |
| WO | WO2012014460 A1 * | 2/2012 |

OTHER PUBLICATIONS

Thelakkat et al. Synthesis and Characterization of Highly Fluorescent Main-Chain Copolyimides Containing Perylene and Quinoxaline Units. Macromolecules 2001, vol. 34, pp. 7441-7447.*

Tress et al. Imbalanced mobilities causing S-shaped IV curves in planar heterojunction organic solar cells. Applied Physics Letters 2011, vol. 98, p. 063301.*

Meiss et al., "Tetrapropyl-tetraphenyl-diindenoperylene derivative as a green absorber for high-voltage stable organic solar cells", 2011, Physical Review, B 83, pp. 16305-1 thru 16305-9.*

Angew. Chem. Int. Ed. 2004, 43, 1528-1531.

Chem. Eur. J. 2001, 7, No. 10, "Novel Perylene Chromophores Obtained by a Facile Oxidative Cyclodehydrogenation Route".

Phys. Status Solidi RRL 4, No. 11, 329-331 (2010) / DOI 10.1002/pssr.201004310.

* cited by examiner

ORGANIC PHOTOELECTRIC DEVICE AND IMAGE SENSOR INCLUDING THE SAME

CROSS-REFERENCE TO RELATED APPLICATION

This application claims priority to and the benefit of Korean Patent Application No. 10-2012-0119252 filed in the Korean Intellectual Property Office on Oct. 25, 2012, the entire contents of which are incorporated herein by reference.

BACKGROUND

1. Field

Example embodiments provide an active layer, and an organic photoelectric device and an image sensor including the same.

2. Description of the Related Art

A photoelectric device refers to a device for converting light into an electrical signal using photoelectric effects. The photoelectric device may include a photodiode and/or a phototransistor, and may be applied to an image sensor and/or a solar cell.

An image sensor including a photodiode requires higher resolution and accordingly a smaller pixel. At present, a silicon photodiode is widely used, but has a problem of deteriorated sensitivity because it has a smaller absorption area due to smaller pixels. Accordingly, an organic photoelectric material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to higher integration.

SUMMARY

Example embodiments provide an organic photoelectric device that selectively absorbs light in a green wavelength and improves efficiency. Example embodiments also provide an image sensor including the organic photoelectric device.

According to example embodiments, an organic photoelectric device that includes an anode and a cathode facing each other and an active layer interposed between the anode and cathode, wherein the active layer may include a compound represented by the following Chemical Formula 1 and a compound represented by the following Chemical Formula 2.

[Chemical Formula 1]

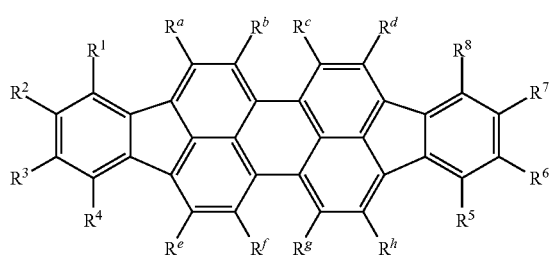

In Chemical Formula 1,
each of $R^a$ to $R^h$ and $R^1$ to $R^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a halogen atom, a halogen-containing group, and a combination thereof,
wherein $R^a$ to $R^h$ and $R^1$ to $R^8$ include at least two adjacent groups of $R^a$ to $R^h$ and $R^1$ to $R^8$ that are linked to each other to form a ring or fused ring.

[Chemical Formula 2]

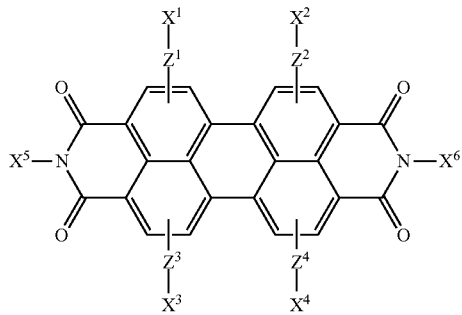

In Chemical Formula 2,
each of $Z^1$ to $Z^4$ are independently one of oxygen (O), nitrogen (N), and sulfur (S), and
each of $X^1$ to $X^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof.

The compound represented by the above Chemical Formula 1 may include a compound represented by the following Chemical Formula 1a.

[Chemical Formula 1a]

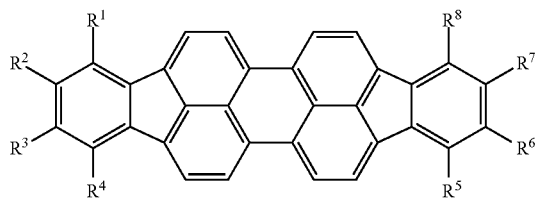

In Chemical Formula 1a,
each of $R^1$ to $R^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a halogen atom, a halogen-containing group, and a combination thereof,
wherein $R^1$ to $R^8$ include at least two adjacent groups of $R^1$ to $R^8$ that are linked to each other to form a ring or fused ring, and
at least one of $R^1$ to $R^8$ is one of a substituted or unsubstituted $C_6$ to $C_{30}$ aryl group, a substituted or unsubstituted $C_3$ to $C_{30}$ heteroaryl group, and a combination thereof.

The compound represented by the above Chemical Formula 1a may include a compound represented by the following Chemical Formula 1aa, a compound represented by the following Chemical Formula 1ab, a compound represented by the following Chemical Formula 1ac, a compound represented by the following Chemical Formula 1ad, or a combination thereof.

[Chemical Formula 1aa]

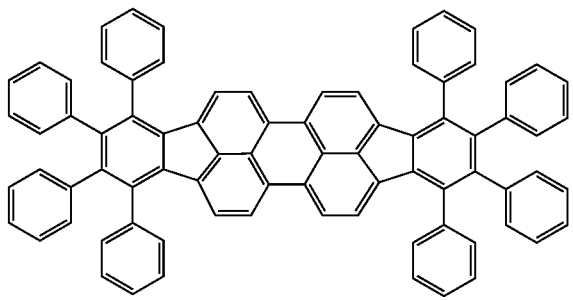

[Chemical Formula 1ab]

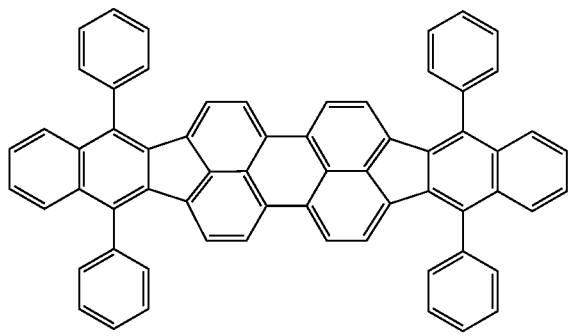

[Chemical Formula 1ac]

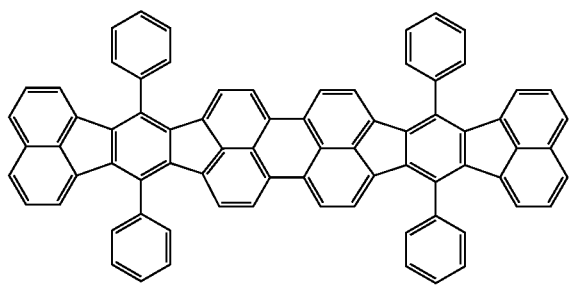

[Chemical Formula 1ad]

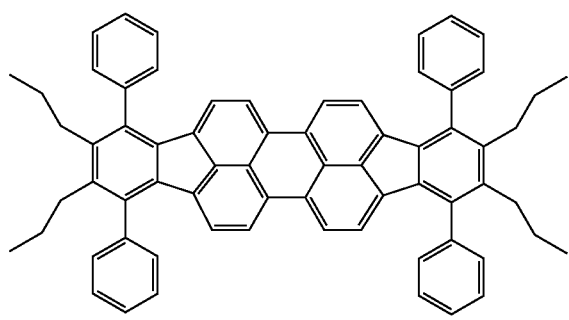

The compound represented by the above Chemical Formula 2 may include a compound represented by the following Chemical Formula 2a.

[Chemical Formula 2a]

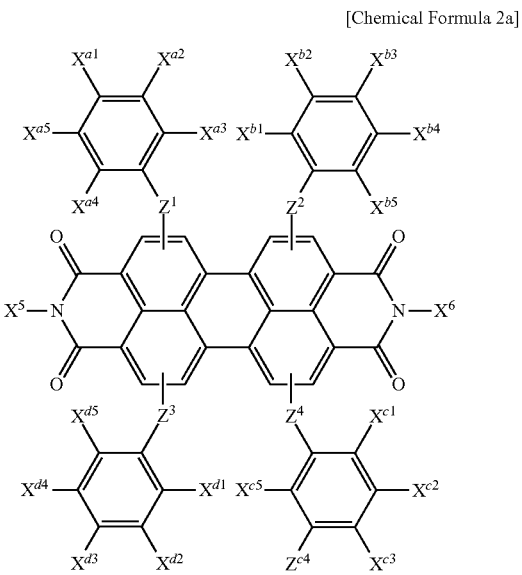

In Chemical Formula 2a, each of $Z^1$ to $Z^4$ are independently one of oxygen (O), nitrogen (N), and sulfur (S), each of $X^{a1}$ to $X^{a5}$, $X^{b1}$ to $X^{b5}$, $X^{c1}$ to $X^{c5}$, and $X^{d1}$ to $X^{d5}$ are independently one of hydrogen, a substituted or unsubstituted $C_1$ to $C_{30}$ alkyl group, a substituted or unsubstituted $C_6$ to $C_{30}$ aryl group, a halogen atom, a halogen-containing group, and a combination thereof, and each of $X^5$ and $X^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof.

The compound represented by the above Chemical Formula 2a may include a compound represented by the following Chemical Formula 2aa, a compound represented by the following Chemical Formula 2ab, or a combination thereof.

[Chemical Formula 2aa]

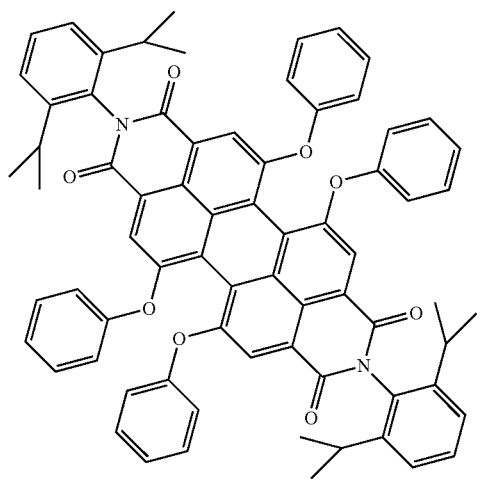

[Chemical Formula 2ab]

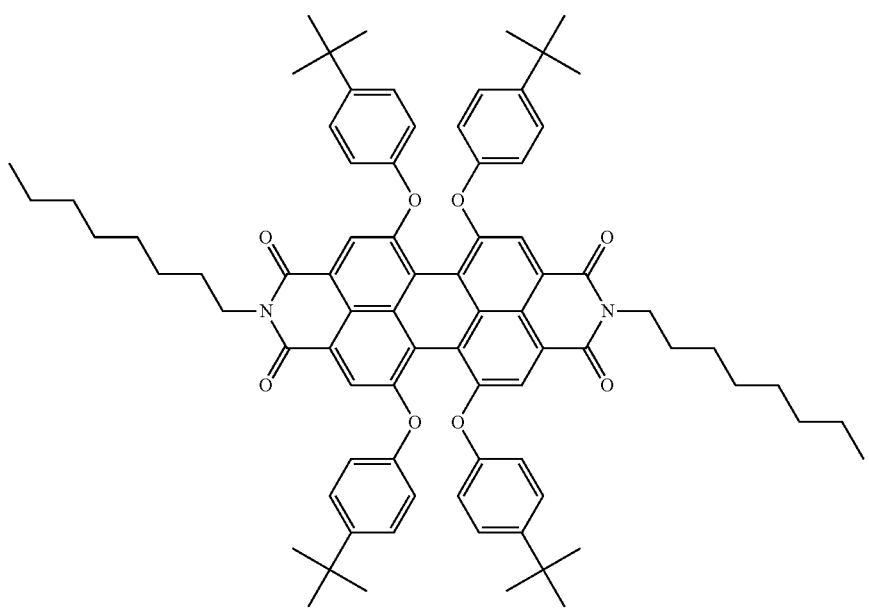

The compound represented by the above Chemical Formula 1 may be a p-type semiconductor, and the compound represented by the above Chemical Formula 2 may be an n-type semiconductor.

The active layer may selectively absorb light in a green wavelength.

The active layer may have a maximum absorption peak in a wavelength region of about 500 nm to about 600 nm.

The active layer may have a full width at half maximum (FWHM) of about 50 nm to about 100 nm in a light-absorption curved line.

The active layer may include a p-type layer including the compound represented by the above Chemical Formula 1 and an n-type layer including the compound represented by the above Chemical Formula 2.

The active layer may include an intrinsic layer including the compound represented by the above Chemical Formula 1 and the compound represented by the above Chemical Formula 2 at a ratio of about 1:100 to about 100:1.

The active layer may include an intrinsic layer including the compound represented by the above Chemical Formula 1 and the compound represented by the above Chemical Formula 2 at a ratio of about 1:10 to 10:1.

The active layer may further include a p-type layer including the compound represented by the above Chemical Formula 1.

The active layer may further include an n-type layer including the compound represented by the above Chemical Formula 2.

The active layer may further include a p-type layer on one side of the intrinsic layer and including the compound represented by the above Chemical Formula 1, and an n-type layer on the other side of the intrinsic layer and including the compound represented by the above Chemical Formula 2.

The organic photoelectric device may further include a charge auxiliary layer between at least one of the anode and the active layer and the cathode and the active layer.

According to example embodiments, an image sensor may include the organic photoelectric device.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
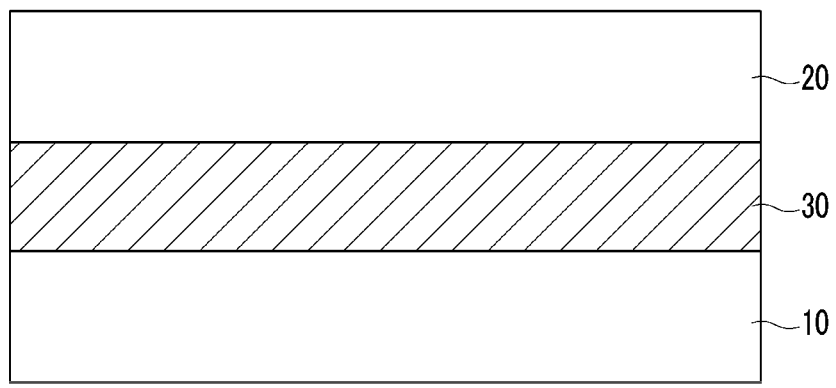
FIG. 1 is a cross-sectional view showing an organic photoelectric device according to example embodiments.

The present disclosure will be described more fully hereinafter with reference to the accompanying drawings, in which example embodiments of this disclosure are shown. This disclosure may, however, be embodied in many different forms and is not construed as limited to the example embodiments set forth herein.

As used herein, when a definition is not otherwise provided, the term "substituted" refers to one substituted with at least a functional group selected from a halogen atom (F, Br, Cl, or I), a hydroxy group, an alkoxy group, a nitro group, a cyano group, an amino group, an azido group, an amidino group, an hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_4$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound.

As used herein, when specific definition is not otherwise provided, the term "hetero" refers to one including 1 to 3 heteroatoms selected from nitrogen (N), oxygen (O), sulfur (S), and phosphorus (P).

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Parts having no relationship with the description are omitted for clarity, and the same or similar constituent elements are indicated by the same reference numeral throughout the specification.

It will be understood that, although the terms "first", "second", etc. may be used herein to describe various elements, components, regions, layers and/or sections, these elements, components, regions, layers and/or sections are not to be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments are not to be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, is to be interpreted as having a meaning that is consistent with their meaning in the context of the relevant art and will not be interpreted in an idealized or overly formal sense unless expressly so defined herein.

FIG. 1 is a cross-sectional view showing an organic photoelectric device according to example embodiments.

Referring to FIG. 1, an organic photoelectric device 100 according to example embodiments includes an anode 10 and cathode 20 facing each other, and an active layer 30 interposed between the anode 10 and cathode 20. FIG. 1 shows that the anode 10 is positioned under the active layer 30, while the cathode 20 is positioned on the active layer 30. However, the cathode 20 may be positioned under the active layer 30, and the anode 10 may be positioned on the active layer 30.

One of the anode 10 and cathode 20 may be made of, for example, a conductive oxide (e.g., indium tin oxide (ITO) or indium zinc oxide (IZO)), and the other may be made of, for example, an opaque conductor (e.g., aluminum (Al)). Alternatively, both the anode 10 and cathode 20 may be made of a transparent conductor (e.g., indium tin oxide (ITO) and/or indium zinc oxide (IZO)), or an opaque (semi-transparent) conductor (e.g., aluminum (Al) and/or silver (Ag)).

The active layer 30 may include a p-type semiconductor material and an n-type semiconductor material to form a pn junction, and receives external light, generates excitons, and separates the excitons into holes and electrons.

The active layer 30 may include a compound represented by the following Chemical Formula 1 and a compound represented by the following Chemical Formula 2.

[Chemical Formula 1]

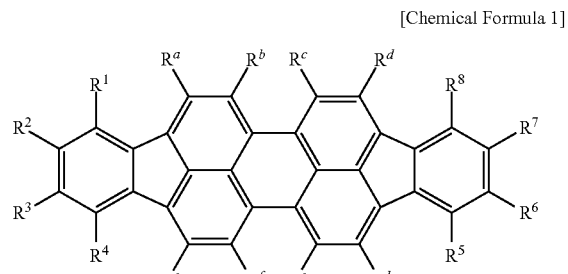

In Chemical Formula 1, each of $R^a$ to $R^h$ and $R^1$ to $R^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a halogen atom, a halogen-containing group, and a combination thereof, wherein $R^a$ to $R^h$ and $R^1$ to $R^8$ may include at least two adjacent groups of $R^a$ to $R^h$ and $R^1$ to $R^8$ that are linked to each other to form a ring or fused ring.

[Chemical Formula 2]

In Chemical Formula 2, each of $Z^1$ to $Z^4$ are independently one of oxygen (O), nitrogen (N), and sulfur (S), and each of $X^1$ to $X^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof.

The compound represented by the above Chemical Formula 1 may include, for example, a compound represented by the following Chemical Formula 1a.

[Chemical Formula 1a]

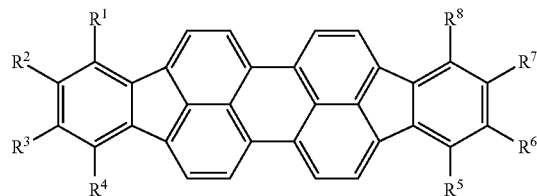

In Chemical Formula 1a, each of $R^1$ to $R^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a halogen atom, a halogen-containing group, and a combination thereof, wherein $R^1$ to $R^8$ may include at least two adjacent groups of $R^1$ to $R^8$ that are linked to each other to form a ring or fused ring.

At least one of $R^1$ to $R^8$ is one of a substituted or unsubstituted $C_6$ to $C_{30}$ aryl group, a substituted or unsubstituted $C_3$ to $C_{30}$ heteroaryl group, and a combination thereof.

The compound represented by the above Chemical Formula 1a may include, for example, a compound represented by the following Chemical Formula 1aa, a compound represented by the following Chemical Formula 1ab, a compound represented by the following Chemical Formula 1ac, a compound represented by the following Chemical Formula 1ad, or a combination thereof.

[Chemical Formula 1aa]

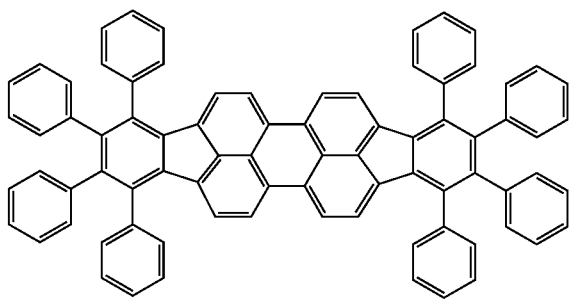

[Chemical Formula 1ab]

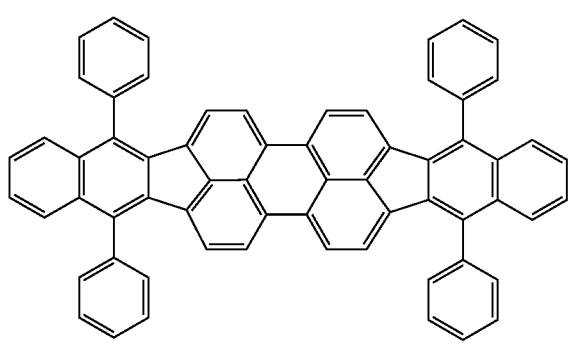

[Chemical Formula 1ac]

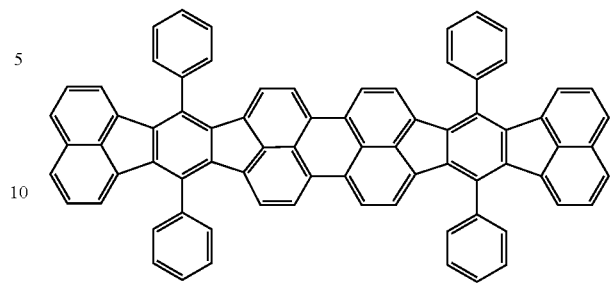

[Chemical Formula 1ad]

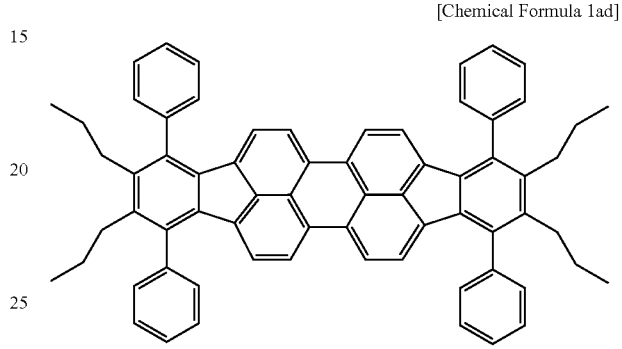

The compound represented by the above Chemical Formula 2 may include, for example, a compound represented by the following Chemical Formula 2a.

[Chemical Formula 2a]

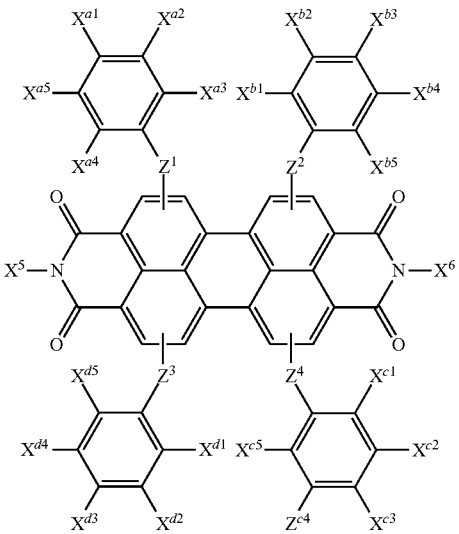

In Chemical Formula 2a, each of $Z^1$ to $Z^4$ are independently one of oxygen (O), nitrogen (N), and sulfur (S), each of $X^{a1}$ to $X^{a5}$, $X^{b1}$ to $X^{b5}$, $X^{c1}$ to $X^{c5}$, and $X^{d1}$ to $X^{d5}$ are independently one of hydrogen, a substituted or unsubstituted $C_1$ to $C_{30}$ alkyl group, a substituted or unsubstituted $C_6$ to $C_{30}$ aryl group, a halogen atom, a halogen-containing group, and a combination thereof, wherein $X^{a1}$ to $X^{a5}$, $X^{b1}$ to $X^{b5}$, $X^{c1}$ to $X^{c5}$, and $X^{d1}$ to $X^{d5}$ may include at least two adjacent groups of $X^{a1}$ to $X^{a5}$, $X^{b1}$ to $X^{b5}$, $X^{c1}$ to $X^{c5}$, and $X^{d1}$ to $X^{d5}$ that are linked to each other to form a ring or fused ring, and each of $X^5$ and $X^6$ are independently hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof.

The compound represented by the above Chemical Formula 2a may include, for example a compound represented by the following Chemical Formula 2aa, a compound represented by the following Chemical Formula 2ab, or a combination thereof.

in a green wavelength, and may have a maximum absorption peak in a wavelength region ranging from about 500 nm to about 600 nm.

The active layer including the compounds represented by the above Chemical Formulae 1 and 2 may have a full width at half maximum (FWHM) ranging from about 50 nm to about 100 nm in a light-absorption curved line. Herein, the full width at half maximum is a wavelength width corresponding to a half of maximum light-absorption. When the

[Chemical Formula 2aa]

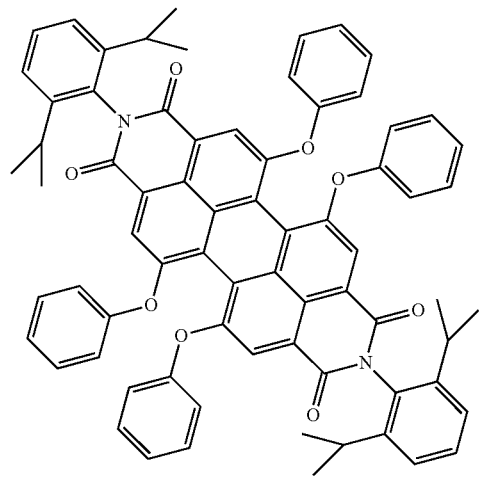

[Chemical Formula 2ab]

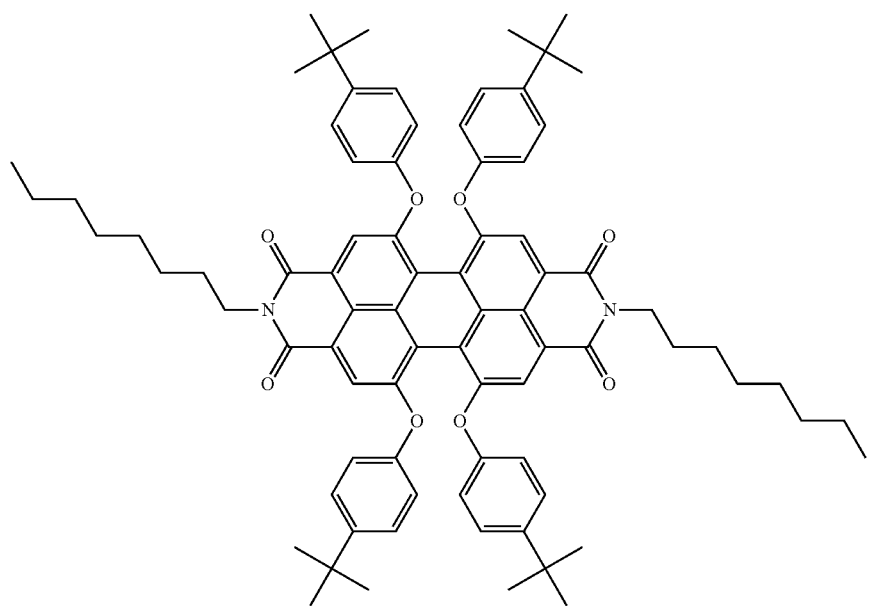

The compound represented by the above Chemical Formula 1 may be a p-type semiconductor, and the compound represented by the above Chemical Formula 2 may be an n-type semiconductor.

The compound represented by the above Chemical Formula 1 and the compound represented by the above Chemical Formula 2 may have a bandgap of about 1.5 eV to 3.5 eV, respectively. Within the range, the compounds may have a bandgap of about 1.8 eV to 2.5 eV. When p-type and n-type semiconductor materials in an active layer respectively have a bandgap within the range, the active layer may absorb light full width at half maximum is relatively small, light in a narrow wavelength region is selectively absorbed, increasing wavelength selectivity. The active layer has a full width at half maximum within the range, and may have relatively high selectivity for a green wavelength region.

The compounds represented by the above Chemical Formulae 1 and 2 have a LUMO energy level difference ranging from about 0.0 eV to 0.7 eV. The LUMO energy level difference may be about 0.3 eV to 0.5 eV within the range. When the p-type and n-type semiconductor materials in an active layer have a LUMO energy level difference within the range, external quantum efficiency (EQE) may be improved and effectively adjusted depending on a bias applied thereto.

The active layer 30 may be a single layer or multilayer. The active layer 30 may be, for example, an intrinsic layer (I layer) or various combinations of p-type layer/n-type layer, p-type layer/I layer, I layer/n-type layer, and p-type layer/I layer/n-type layer.

The intrinsic layer may include the compound represented by the above Chemical Formula 1 and the compound represented by the above Chemical Formula 2 at a ratio of about 1:100 to about 100:1. The two compounds may be included in a ratio ranging from about 1:50 to about 50:1, for example, about 1:10 to about 10:1, or about 1:1. When the p-type and n-type semiconductors have a composition ratio within the range, an exciton may be effectively generated, and a pn junction may be effectively formed.

The p-type layer may include the compound represented by the above Chemical Formula 1, and the n-type layer may include the compound represented by the above Chemical Formula 2.

The active layer 30 may have a thickness ranging from about 1 nm to about 500 nm. The active layer 30 may have a thickness of about 5 nm to about 300 nm within the range. When the active layer 30 has a thickness within the range, the active layer may effectively absorb light, effectively separate and transmit holes and electrons, effectively improving photoelectric conversion efficiency.

In the organic photoelectric device 100, when light is incident from the anode 10 and/or the cathode 20, and when the active layer 30 absorbs light having a predetermined or given wavelength region, excitons may be generated from the inside. The excitons are separated into holes and electrons at the active layer 30, and the separated holes are transferred to an anode 10 and the separated electrons are transferred to a cathode 20 so as to flow a current in the organic photoelectric device.

Figure 2:
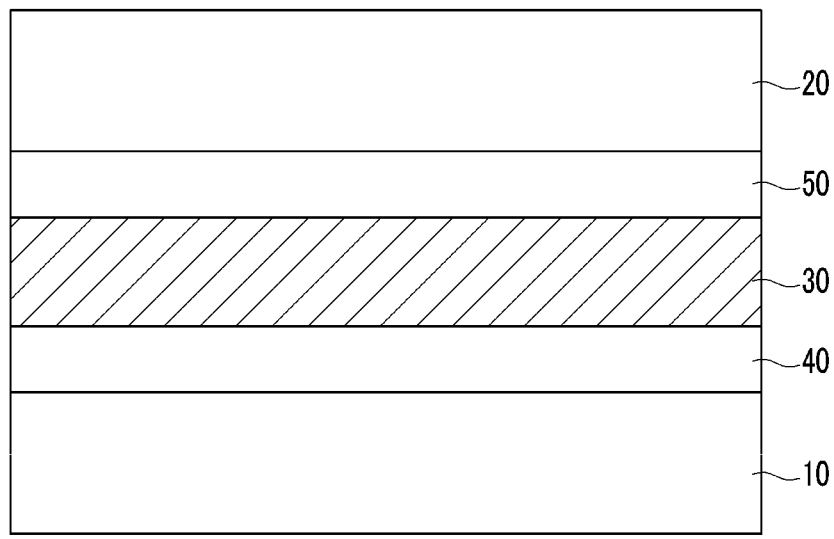
FIG. 2 is a cross-sectional view showing an organic photoelectric device according to example embodiments.

FIG. 2 is a cross-sectional view showing an organic photoelectric device according to example embodiments.

Referring to FIG. 2, an organic photoelectric device 100 according to example embodiments may include the anode 10 and cathode 20 facing each other, and an active layer 30 interposed between the anode 10 and cathode 20, and these are all the same as described in example embodiments as illustrated in FIG. 1.

However, the organic photoelectric device 100 according to example embodiments may further include charge auxiliary layers 40 and 50 respectively between the anode 10 and active layer 30 and the cathode 20 and active layer 30. The charge auxiliary layers 40 and 50 may facilitate the transportation of holes and electrons separated from the active layer 30, so as to increase efficiency.

The charge auxiliary layer 40 may be at least one selected from a hole injection layer (HIL) for facilitating hole injection, a hole transport layer (HTL) for facilitating hole transport, an electron blocking layer (EBL) for preventing or inhibiting electron transport, and the charge auxiliary layer 50 may be at least one selected from an electron injection layer (EIL) for facilitating electron injection, an electron transport layer (ETL) for facilitating electron transport, and a hole blocking layer (HBL) for preventing or inhibiting hole transport.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis (4-methoxyphenyl)-benzidine (TPD), 4-bis[N-(1-naphthyl)-N-phenyl-amino]phenyl (α-NPD), m-MTDATA, 4,4',4"-tris (N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole (polypyrrole), N,N,N',N'-tetrakis(4-methoxyphenyl)-benzidine (TPD), 4-bis[N-(1-naphthyl)-N-phenyl-amino] biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 50 may be omitted. The organic photoelectric device may be applied to various fields, for example, a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
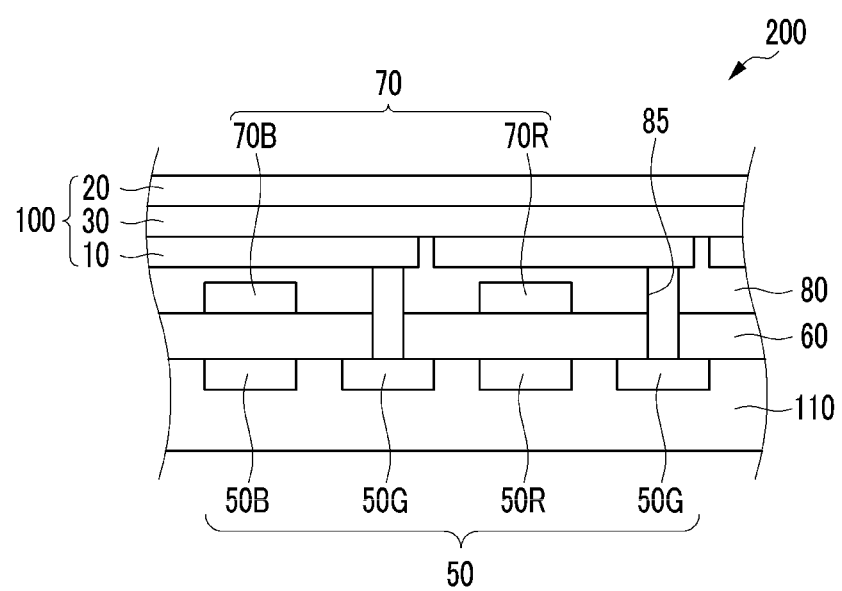
FIG. 3 is a cross-sectional view showing an organic CMOS image sensor according to example embodiments.

FIG. 3 is a cross-sectional view showing an organic CMOS image sensor according to example embodiments.

FIG. 3 illustrates adjacent blue, green, and red pixels, but is not limited thereto. Hereinafter, a constituent element including "B" in the reference symbol refers to a constituent element included in the blue pixel, a constituent element including "G" refers to a constituent element included in the green pixel, and a constituent element including "R" in the reference symbol refers to a constituent element included in the red pixel.

Referring to FIG. 3, an organic CMOS image sensor 200 includes a semiconductor substrate 110 integrated with a photo-sensing device 50 and a transmission transistor (not shown), a lower insulation layer 60, color filters 70B, and 70R, an upper insulation layer 80, and an organic photoelectric device 100.

The semiconductor substrate 110 may be a silicon substrate, and is integrated with the photo-sensing device 50 and a transmission transistor (not shown). The photo-sensing device 50 may be a photodiode. The photo-sensing device 50 and the transmission transistor may be integrated in each pixel, and as shown in the drawing, the photo-sensing device 50 includes a blue pixel photo-sensing device 50B, a green pixel photo-sensing device 50G, and a red pixel photo-sensing device 50R. The photo-sensing device 50 senses light, and the information sensed by the photo-sensing device 50 is transferred by a transmission transistor.

Metal wires (not shown) and pads (not shown) are formed on the semiconductor substrate 110. In order to decrease signal delay, the metal wires and pads may be made of a metal having relatively low resistivity, for example, aluminum (Al), copper (Cu), silver (Ag), and alloys thereof, but is not limited thereto.

A lower insulation layer 60 may be formed on the metal wires and pads. The lower insulation layer 60 may be made of an inorganic insulating material (e.g., silicon oxide and/or silicon nitride), or a low dielectric constant (low K) material (e.g., SiC, SiCOH, SiCO, and SiOF).

The lower insulation layer 60 has a trench (not shown) exposing each photo-sensing device 50B, 50G, and 50R of each pixel. The trench may be filled with fillers.

A color filter 70 may be formed on the lower insulation layer 60. The color filter 70 includes the blue filter 70B formed in the blue pixel, and the red filter 70R filled in the red pixel. In example embodiments, a green filter is not mounted but a green filter may be mounted.

The upper insulation layer 80 may be formed on the color filter 70. The upper insulation layer 80 eliminates a step-difference by the color filters 70 and smoothes the surface. The upper insulation layer 80 and lower insulation layer 60 may include a contact hole (not shown) exposing a pad and a through-hole 85 exposing the photo-sensing device 500 of a green pixel.

The organic photoelectric device 100 is formed on the upper insulation layer 80. The organic photoelectric device 100 includes an anode 10, an active layer 30, and a cathode 20 as described. However, the positions of the anode 10 and cathode 20 may be exchanged with each other. For better understanding and ease of description, the organic photoelectric device 100 according to example embodiments is shown, but it is not limited thereto, and all organic photoelectric devices 100 may be applicable.

Both of the anode 10 and the cathode 20 may be light-transmission electrodes. The active layer 30 includes a p-type semiconductor represented by Chemical Formula 1 and an n-type semiconductor represented by Chemical Formula 2, and selectively absorbs light in a green wavelength region as aforementioned and may replace a color filter of green pixels.

When light enters from the anode 10, the light in a green wavelength region may be mainly absorbed in the active layer 30 and photoelectrically converted, while the light in the rest of the wavelength regions passes the cathode 20 and may be sensed in the photo-sensing device 50.

Hereinafter, the present disclosure is illustrated in more detail with reference to examples. However, these embodiments are examples, and the present disclosure is not limited thereto.

SYNTHESIS EXAMPLES

Synthesis Example 1-1

1.9 g (12.5 mmol) of acenaphthylene is mixed with 5.11 g (13.3 mmol) of tetraphenylcyclopentadienone in 40 ml of xylene, and the mixture is refluxed for 16 hours under an argon atmosphere. The mixture is cooled down to room temperature, and 300 ml of ethanol is added thereto. A precipitate produced therein is filtered. The filtrate is cleaned with ethanol and dried under vacuum. The obtained solid is dissolved in 100 ml of a mixed solvent of acetone/benzene (1:5 v/v), and a $KMnO_4$/acetone solution is added thereto until the solution becomes purple. The $KMnO_4$ is removed by filtering the mixture through a silica gel column, and the solvent is evaporated therefrom. The resultant is dried under vacuum, obtaining a yellow solid.

506 mg (1 mmol) of the yellow solid is dissolved in 40 ml of $CH_2Cl_2$, and another solution prepared by dissolving 1.9 g (11.7 mmol) of $FeCl_3$ in 3 ml of nitromethane is added thereto. The mixture is sufficiently agitated, and 40 ml of methanol is added thereto. A precipitate produced therein is filtered, cleaned with 40 ml of methanol, and dried under a reduced pressure. The obtained product is purified through silica gel column chromatography (eluent: dichloromethane/ petroleum ether mixed in a ratio of 1:1), obtaining a red compound represented by the following Chemical Formula 1 aa. The yield is 90%.

[Chemical Formula 1aa]

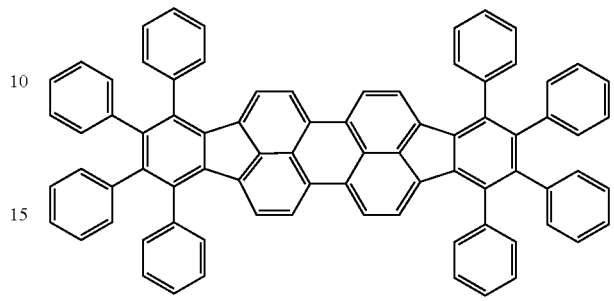

$^1$H NMR (500 MHz, $C_2D_2Cl_4$, 130 8C): d. 7.80 (d, 3J (H, H)). 7.3 (Hz, 4H), 7.30±7.26 (m, 20H), 6.87±6.78 (m, 20 H), 6.55 (d, 3J (H, H)). 7.3 (Hz, 4H); 13C NMR (125 MHz, C2D2Cl4, 130 8C): d, 141.3, 140.2, 137.8, 137.2, 136.8, 134.8, 131.7, 130.5, 128.4, 127.2, 126.9, 125.6, 124.4, 122.2, 121.8; MS (FD): m/z (%): 1008.9 ([M], 100); elemental analysis calc'd (%) for $C_8OH_{48}$ (1009.26): C, 95.21; H, 4.79. found C, 95.73; H, 4.99.

Synthesis Example 1-2

A compound represented by the following Chemical Formula 1ab is synthesized according to the same method as Synthesis Example 1-1 except for using 3.76 g (13.3 mmol) of 1,3-diphenyl-2H-inden-2-one instead of 5.11 g (13.3 mmol) of tetraphenylcyclopentadienone.

[Chemical Formula 1ab]

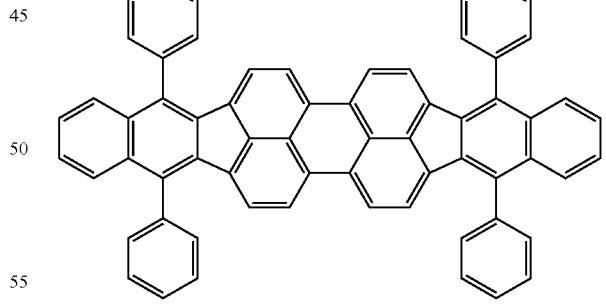

Synthesis Example 1-3

A compound represented by the following Chemical Formula 1ac is synthesized according to the same method as Synthesis Example 1-1 except for using 4.74 g (13.3 mmol) of 7,9-diphenyl-8H-cyclopenta[a]enaphthylen-8-one instead of 5.11 g (13.3 mmol) of tetraphenylcyclopentadienone.

[Chemical Formula 1ac]

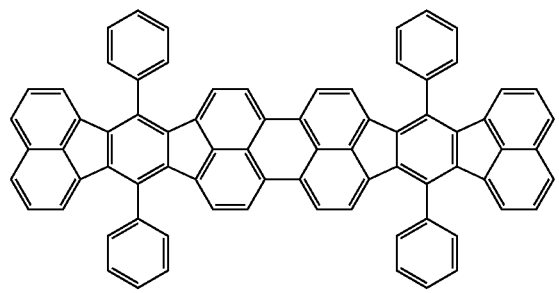

Synthesis Example 1-4

A compound represented by the following Chemical Formula 1ad is synthesized according to the same method as Synthesis Example 1-1 except for using 4.21 g (13.3 mmol) of 2,5-diphenyl-3,4-dipropylcyclopenta-2,4-dienone instead of 5.11 g (13.3 mmol) of tetraphenylcyclopentadienone.

[Chemical Formula 1ad]

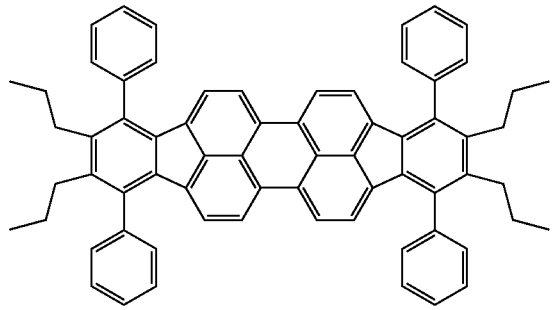

Synthesis Example 2-1

3.92 g (10 mmol) of 3,4,9,10-perylenetetracarboxylic dianhydride is added to a mixed solvent of 100 ml of $H_2O$ and 100 ml of propanol. The mixture is agitated. 2.93 g (40 mmol) of 2,6-diisopropylaniline is dripped into the mixture drop by drop. The resulting mixture is agitated at 70° C. for 12 hours. The agitated mixture is filtered at room temperature, cleaned with $H_2O$ and methanol, and dried, obtaining 3.82 g (7.6 mmol) of N,N'-bis-2,6-diisopropylphenyl-3,4,9,10-perylenetetracarboxylic acid diimide.

3.82 g (7.6 mmol) of the N,N'-bis-2,6-diisopropylphenyl-3,4,9,10-perylenetetracarboxylic acid diimide, 29.2 g (237 mmol) of nitrobenzene, 0.29 g (2.28 mmol) of iodine, and 0.29 g (1.42 mmol) of iodobenzene are dripped into a round flask drop by drop at 80° C. for 2 hours, while the flask is maintained under an argon atmosphere. The mixture is reacted for about 8 hours, agitated for 6 hours, and filtered, obtaining 4.3 g (6.7 mmol) of N,N'-bis-2,6-diisopropylphenyl-1,6,7,12-tetrachloroperylene-3,4,9,10-tetracarboxylic acid diimide.

4.29 g (6.69 mmol) of the bis-2,6-diisopropylphenyl-1,6,7,12-tetrachloroperylene-3,4,9,10-tetracarboxylic acid diimide, 6.03 g (40.1 mmol) of phenol, 5.54 g (40.1 mmol) of $K_2CO_3$, and 30.8 g (3.21 mmol) of NMP are added into a round flask at 140° C. for 8 hours, while the flask is maintained under an argon atmosphere. The mixture is cooled down to room temperature, and 150 ml (8 vol %) of an HCl aqueous solution is slowly added thereto. The mixture is cleaned with water for about 2 hours, filtered, and vacuum-dried. The vacuum-dried product is purified through silica gel column chromatography (eluent: dichloromethane/hexane mixed in a ratio of 3:1), obtaining 6.31 g (5.76 mmol) of N,N'-bis-2,6-diisopropylphenyl-1,6,7,12-tetrakis(phenoxy)perylene-3,4,9,10-tetracarboxylic acid diimide represented by the following Chemical Formula 2aa.

[Chemical Formula 2aa]

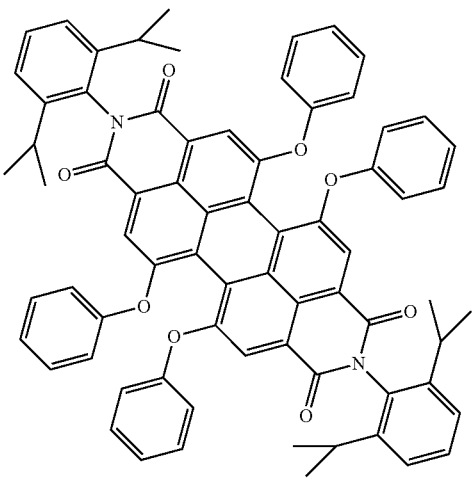

Synthesis Example 2-2

3.92 g (10 mmol) of 3,4,9,10-perylenetetracarboxylic dianhydride is added to a mixed solvent of 100 ml of $H_2O$ and 100 ml of propanol. The mixture is agitated. Then, 2.93 g (40 mmol) of octylamine is added to the agitated mixture drop by drop. The resulting mixture is agitated at 70° C. for 12 hours. The agitated mixture is filtered at room temperature, cleaned with $H_2O$ and methanol, and dried, obtaining 3.82 g (7.6 mmol) of N,N'-dioctyl-3,4,9,10-perylenetetracarboxylic acid diimide.

While a round flask is maintained under an argon atmosphere, 3.82 g (7.6 mmol) of the N,N'-dioctyl-3,4,9,10-perylenetetracarboxylic acid diimide, 29.2 g (237 mmol) of nitrobenzene, 0.29 g (2.28 mmol) of iodine, and 0.29 g (1.42 mmol) of iodobenzene are added to the flask, and 6.14 g (45.5 mmol) of sulfurylchloride is added drop by drop to the mixture while being agitated at 80° C. for 2 hours. After reaction for about 8 hours, 180 ml of methanol is added to the agitated mixture. The resulting mixture is agitated for 6 hours and filtered, obtaining 4.3 g (6.7 mmol) of N,N'-dioctyl-1,6,7,12-tetrachloroperylene-3,4,9,10-tetracarboxylic acid diimide.

While a round flask is maintained under an argon atmosphere, 4.29 g (6.69 mmol) of the N,N'-dioctyl-1,6,7,12-tetrachloroperylene-3,4,9,10-tetracarboxylic acid diimide, 6.03 g (40.1 mmol) of 4-t-butylphenol, 5.54 g (40.1 mmol) of $K_2CO_3$, and 30.8 g (3.21 mmol) of NMP are added to the flask and agitated at 140° C. for 8 hours. The mixture is cooled down to room temperature, and 150 ml (8 vol %) of a HCl aqueous solution is slowly added thereto. The mixture is cleaned with water for about 2 hours, filtered, and vacuum-dried. The vacuum-dried product is purified through silica gel column chromatography (eluent: dichloromethane/hexane mixed in a ratio of 3:1), obtaining 6.31 g (5.76 mmol) of N,N'-dioctyl-1,6,7,12-tetrakis(4-t-butylphenoxy)perylene-3,4,9,10-tetracarboxylic acid diimide represented by the following Chemical Formula 2ab.

[Chemical Formula 2ab]

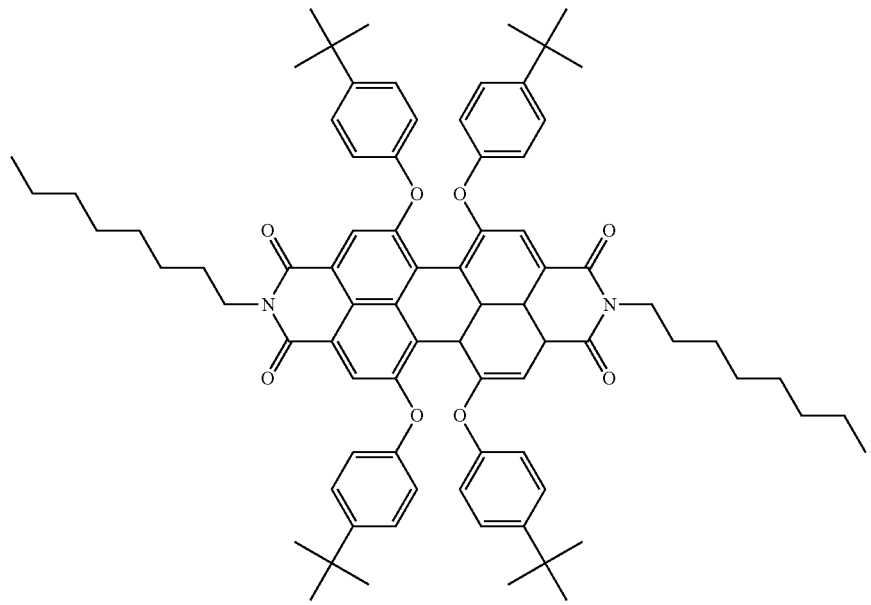

Comparative Synthesis Example 1

3.92 g (10 mmol) of 3,4,9,10-perylenetetracarboxylic dianhydride is added to a mixed solvent of 100 ml of $H_2O$ and 100 ml of propanol. 2.93 g (40 mmol) of methylamine is added drop by drop to the mixture. The resulting mixture is agitated at 70° C. for 12 hours. The agitated mixture is filtered at room temperature, cleaned with $H_2O$ and methanol, and dried, obtaining 3.82 g (7.6 mmol) of N,N'-dimethyl-3,4,9,10-perylenetetracarboxylic acid diimide represented by the following Chemical Formula B.

[Chemical Formula B]

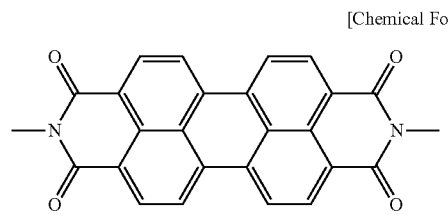

Evaluation 1: Light-Absorption Characteristic

The compounds according to Synthesis Examples 1-1 to 2-2 and Comparative Synthesis Example 1 are evaluated regarding light-absorption characteristics depending on a wavelength.

The light-absorption characteristics may be evaluated by dissolving the compounds according to Synthesis Examples 1-1 to 2-2 and Comparative Synthesis Example 1 in an organic solvent (e.g., chloroform) or vacuum-depositing them on a transparent glass substrate, and radiating ultraviolet (UV)-visible (UV-Vis rays) rays thereto using a Cary 5000 UV spectroscope (Varian Inc.).

Figure 4A:
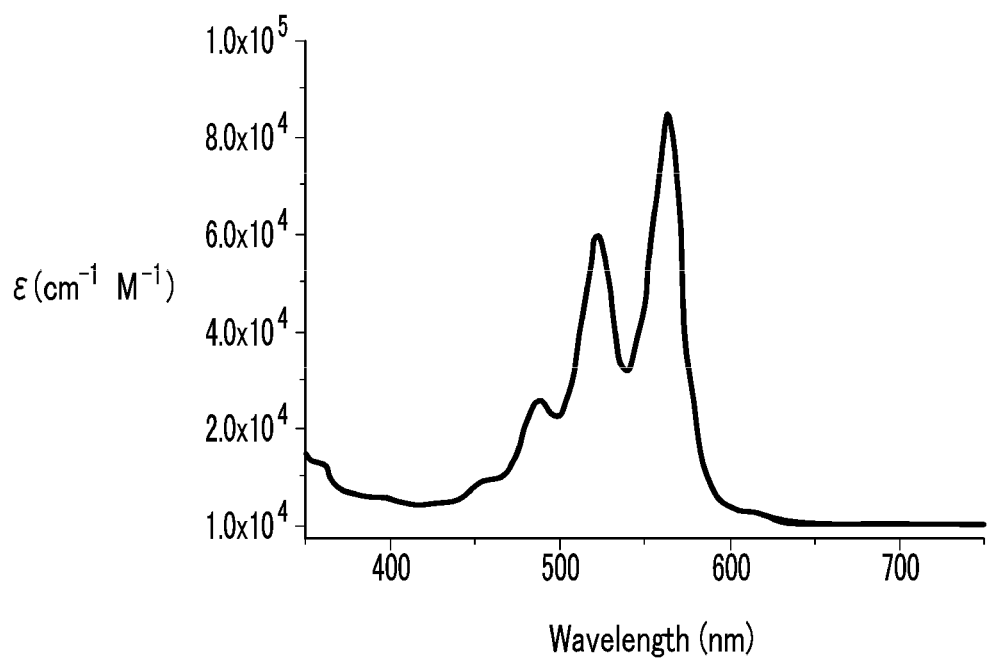
FIG. 4A is a graph showing light-absorption characteristics of the compound according to Synthesis Example 1-1 in a solution state, depending on a wavelength.
Figure 4B:
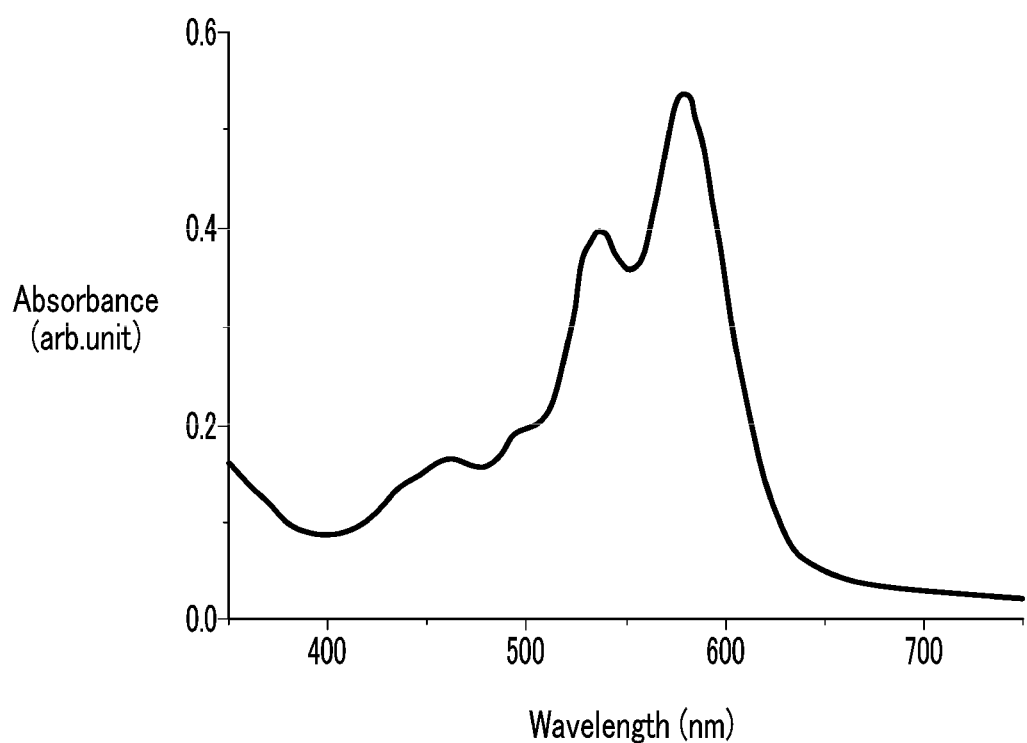
FIG. 4B is a graph showing light-absorption characteristics of the compound according to Synthesis Example 1-1 in a thin layer state, depending on a wavelength.
Figure 5:
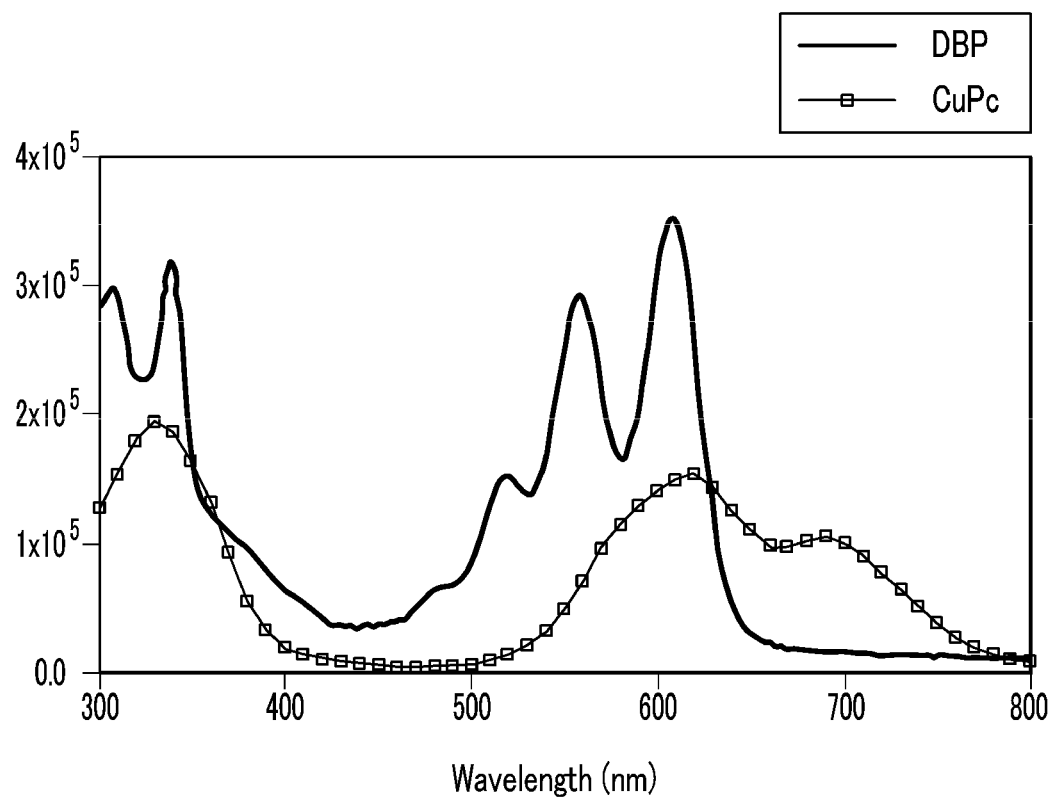
FIG. 5 is a graph showing light-absorption characteristics of the compound according to Synthesis Example 1-2 in a thin layer state, depending on a wavelength.
Figure 6:
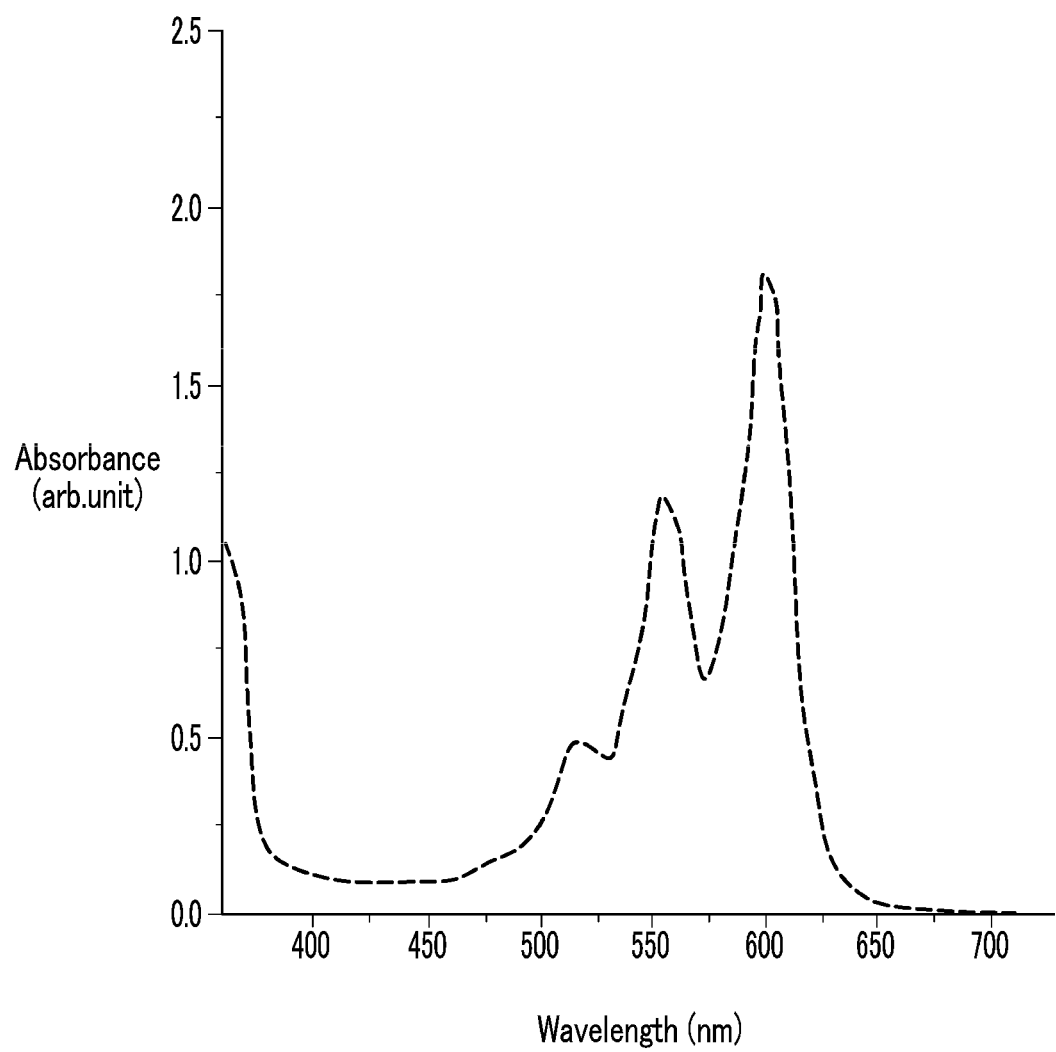
FIG. 6 is a graph showing light-absorption characteristics of the compound according to Synthesis Example 1-3 in a thin layer state, depending on a wavelength.
Figure 7:
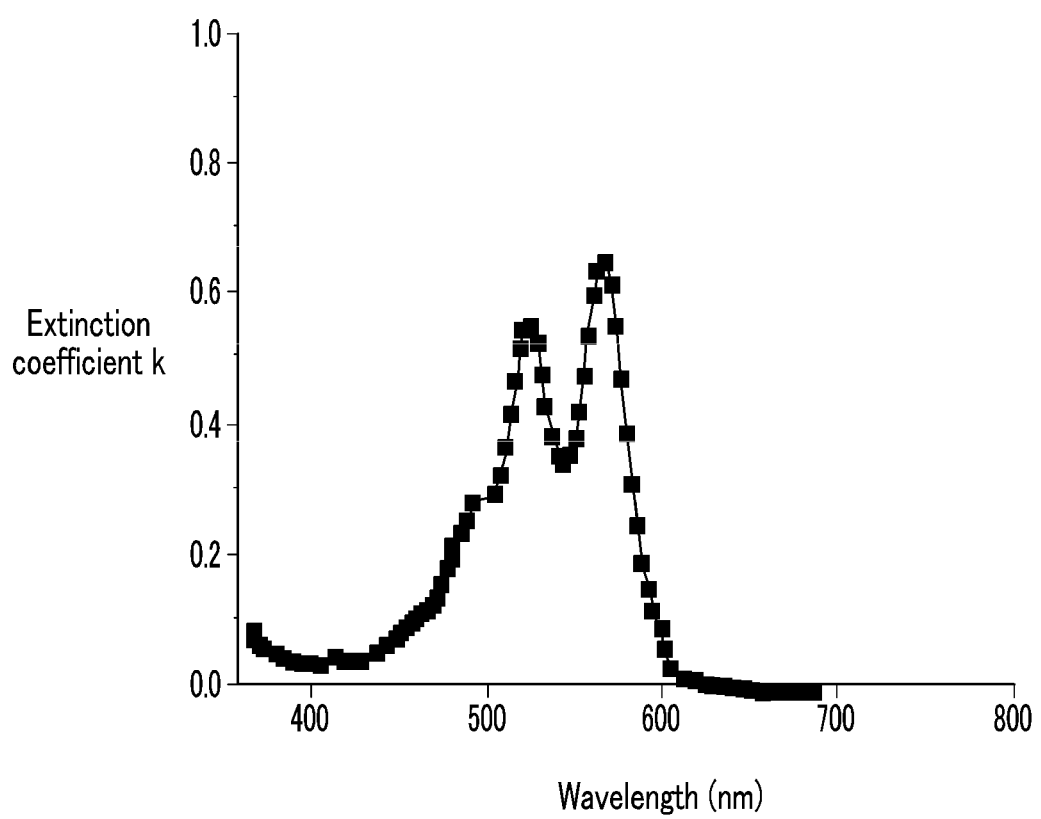
FIG. 7 is a graph showing light-absorption characteristics of the compound according to Synthesis Example 1-4 in a thin layer state, depending on a wavelength.
Figure 8A:
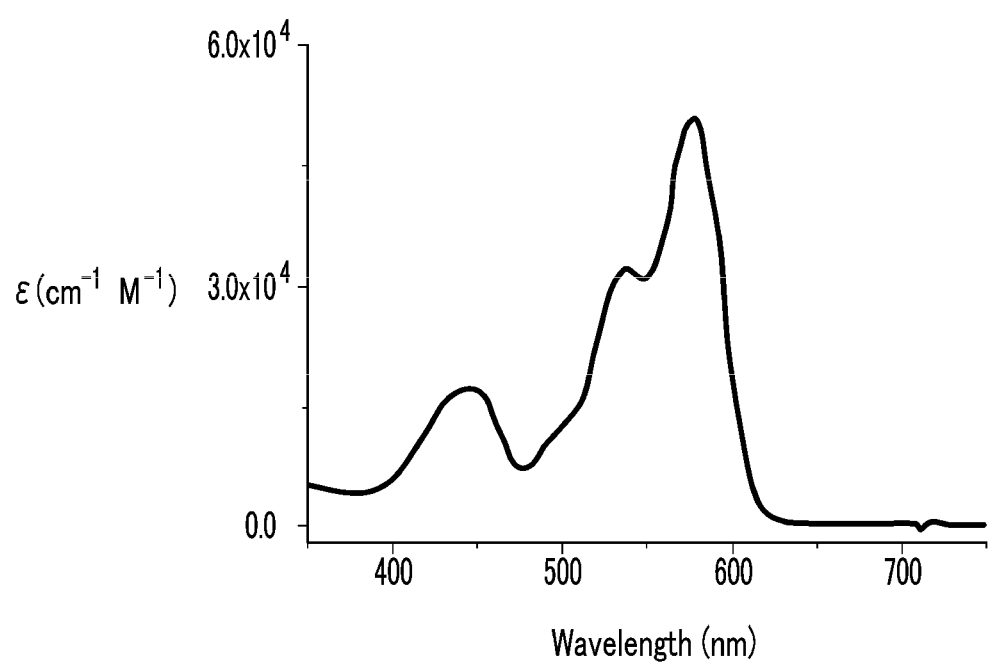
FIG. 8A is a graph showing light-absorption characteristics of the compound according to Synthesis Example 2-1 in a solution state, depending on a wavelength.
Figure 8B:
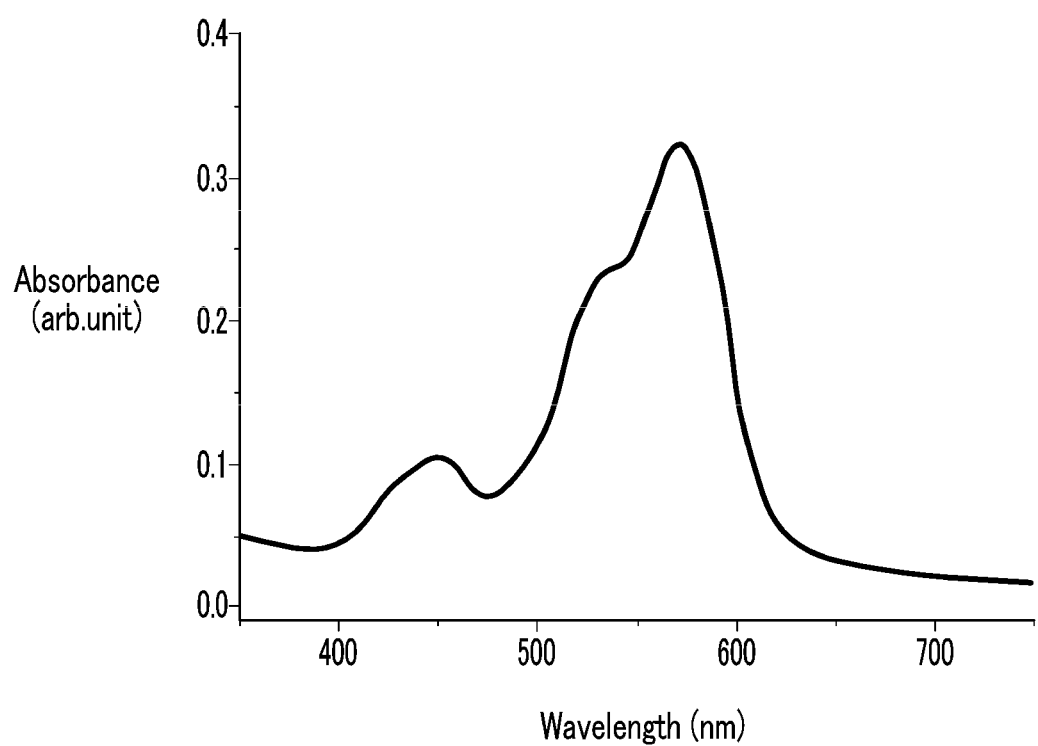
FIG. 8B is a graph showing light-absorption characteristics of the compound according to Synthesis Example 2-1 in a thin layer state, depending on a wavelength.
Figure 9A:
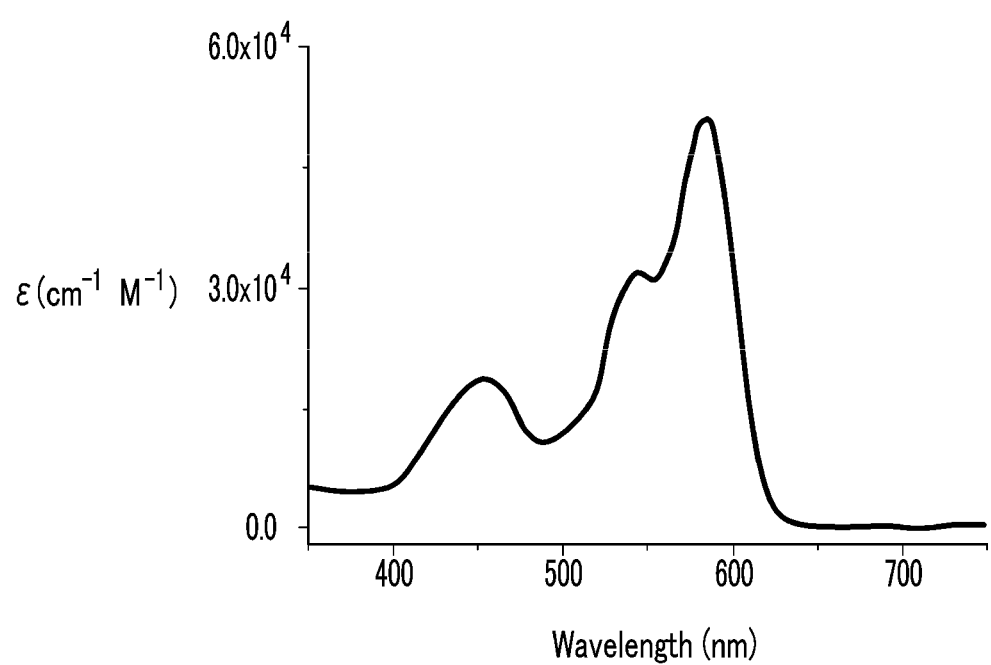
FIG. 9A is a graph showing light-absorption characteristics of the compound according to Synthesis Example 2-2 in a solution state, depending on a wavelength.
Figure 9B:
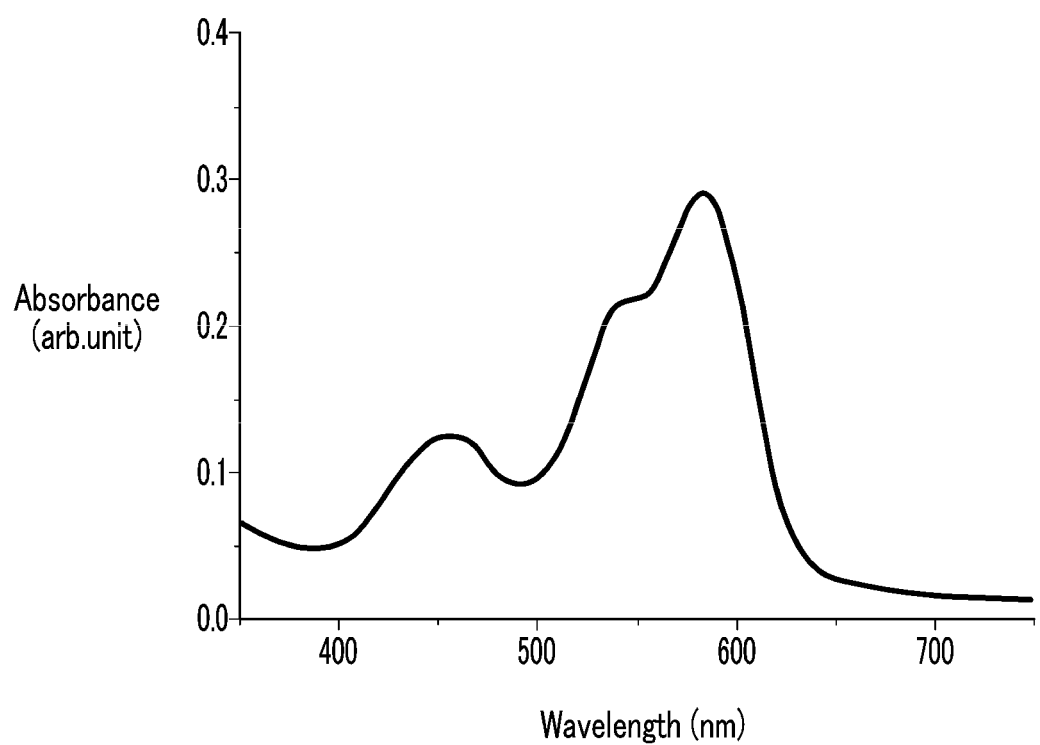
FIG. 9B is a graph showing light-absorption characteristics of the compound according to Synthesis Example 2-2 in a thin layer state, depending on a wavelength.
Figure 10:
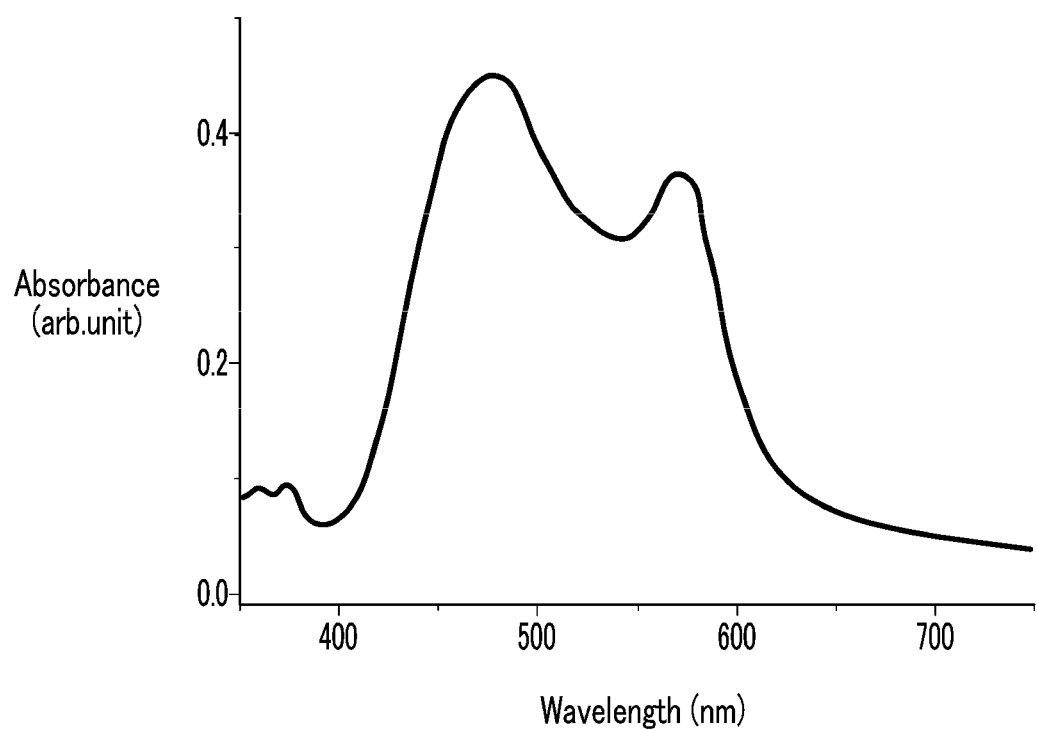
FIG. 10 is a graph showing light-absorption characteristics of the compound according to Comparative Synthesis Example 1 in a thin layer state (50 nm), depending on a wavelength.
Figure 11:
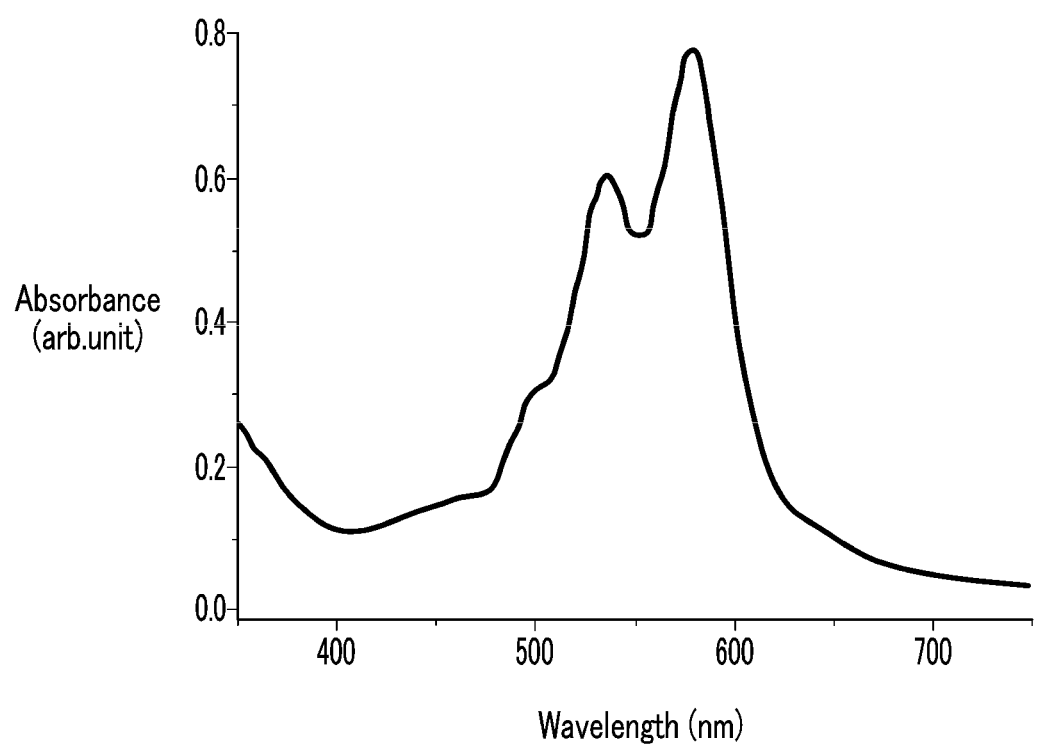
FIGS. 11 to 18 are graphs showing light-absorption characteristics of active layers of the organic photoelectric devices according to Examples 1-1 to 3 and Comparative Examples 1 to 3, respectively.
Figure 12:
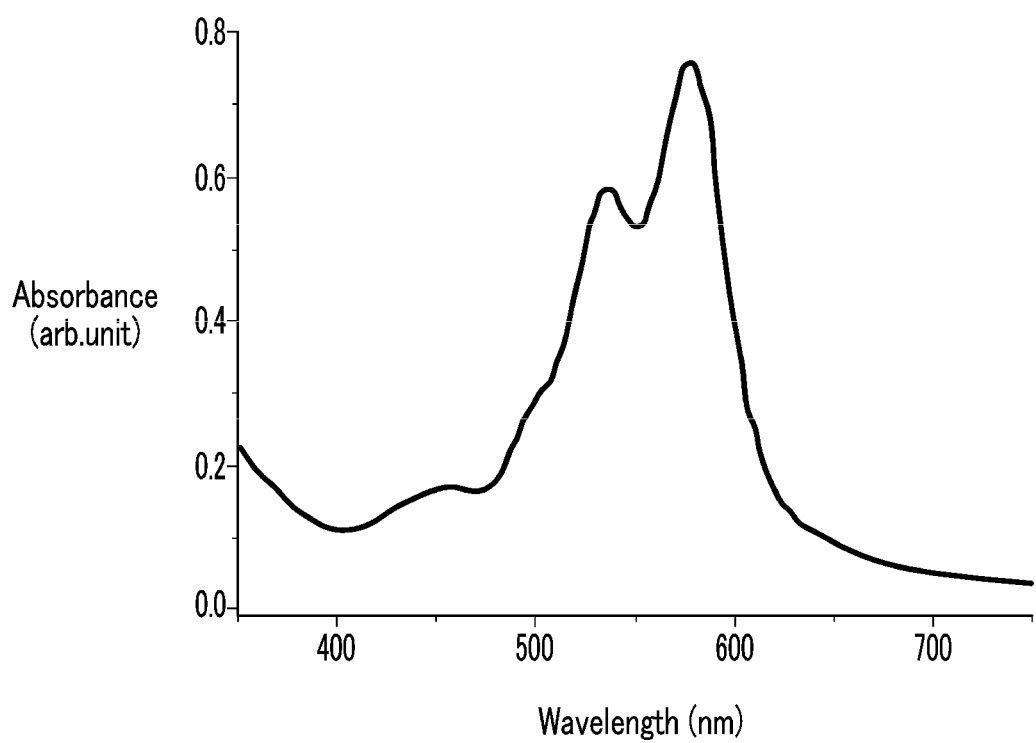
Figure 13:
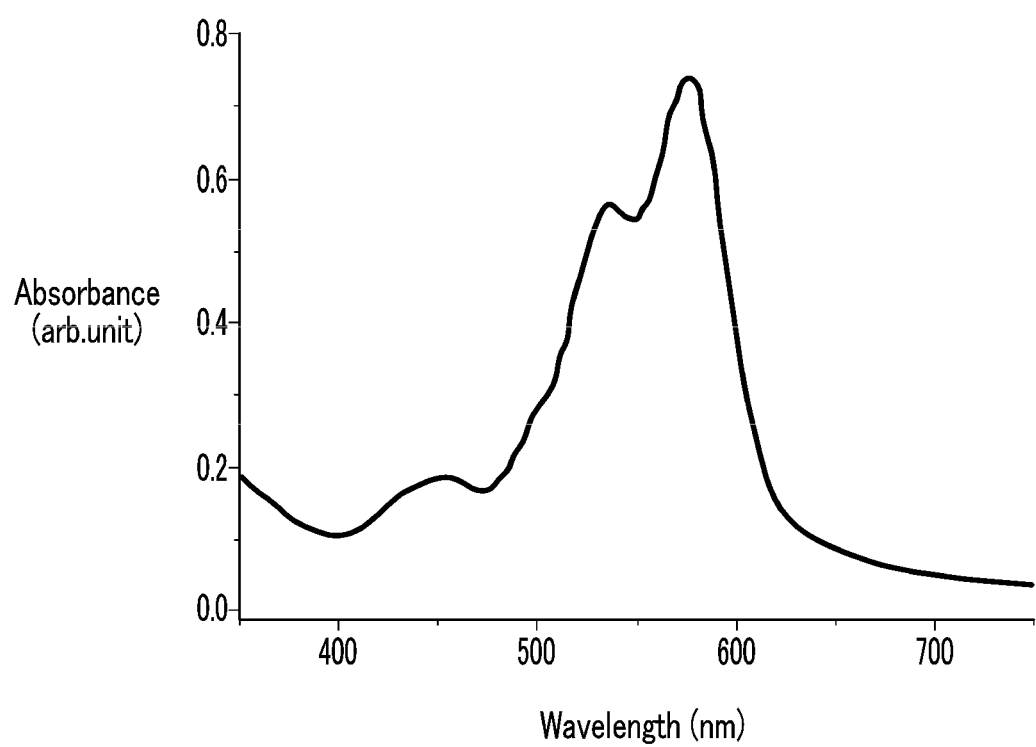
Figure 14:
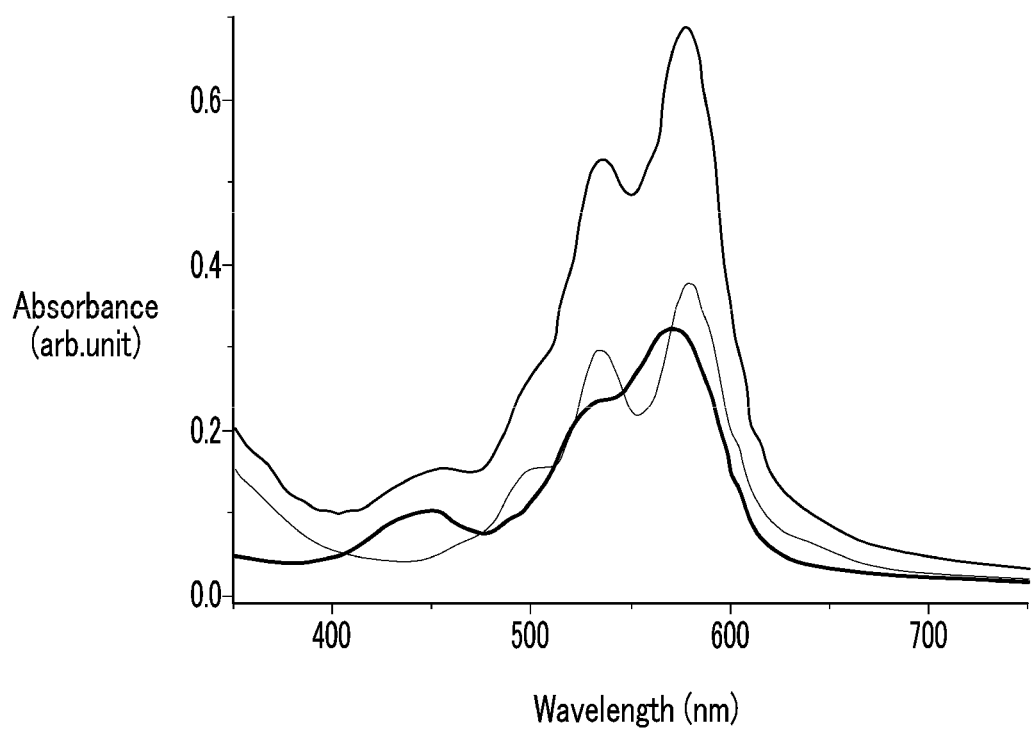
Figure 15:
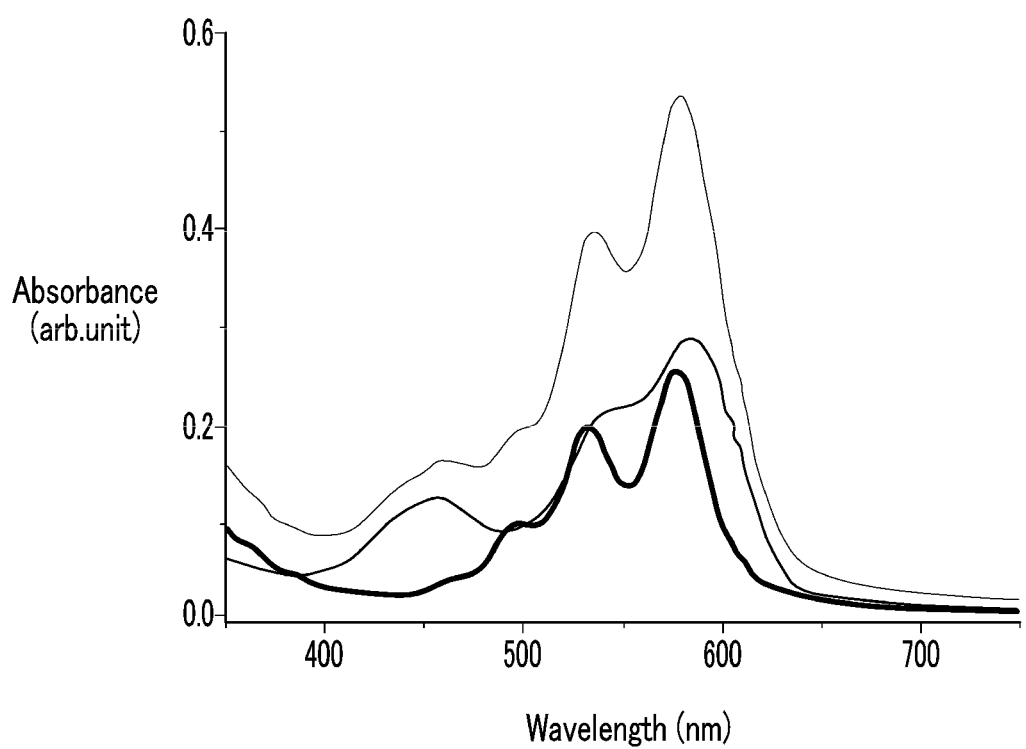

FIG. 4A is a graph showing light-absorption characteristics of the compound according to Synthesis Example 1-1 in a solution state, depending on a wavelength, FIG. 4B is a graph showing light-absorption characteristics of the compound according to Synthesis Example 1-1 in a thin layer state, depending on a wavelength, FIG. 5 is a graph showing light-absorption characteristics of the compound according to Synthesis Example 1-2 in a thin layer state, depending on a wavelength, FIG. 6 is a graph showing light-absorption characteristics of the compound according to Synthesis Example 1-3 in a thin layer state, depending on a wavelength, FIG. 7 is a graph showing light-absorption characteristics of the compound according to Synthesis Example 1-4 in a thin layer state, depending on a wavelength, FIG. 8A is a graph showing light-absorption characteristics of the compound according to Synthesis Example 2-1 in a solution state, depending on a wavelength, FIG. 8B is a graph showing light-absorption characteristics of the compound according to Synthesis Example 2-1 in a thin layer state, depending on a wavelength, FIG. 9A is a graph showing light-absorption characteristics of the compound according to Synthesis Example 2-2 in a solution state, depending on a wavelength, FIG. 9B is a graph showing light-absorption characteristics of the compound according to Synthesis Example 2-2 in a thin layer state, depending on a wavelength, and FIG. 10 is a graph showing light-absorption characteristics of the compound according to Comparative Synthesis Example 1 in a thin layer state (50 nm), depending on a wavelength.

Referring to FIGS. 4A to 10, the compounds according to Synthesis Examples 1-1 to 2-2 in a solution state and/or a thin layer state have a maximum absorption peak in a wavelength region of about 500 nm to about 600 nm, and may selectively absorb a light in a green wavelength region. In addition, the compounds have a sharp peak in the wavelength region and may increase sensitivity and color purity. On the contrary, the maximum absorption peak of the compound according to Comparative Synthesis Example 1 is not in a wavelength region of about 500 nm to about 600 nm.

Organic Photoelectric Device

EXAMPLE 1-1

ITO is sputtered on a glass substrate to form about a 100 nm-thick anode, and a 30 nm-thick molybdenum oxide (MoOx) thin layer on a charge auxiliary layer is formed thereon. A p/i/n active layer is formed by depositing a 30 nm-thick p-type layer including the compound according to Synthesis Example 1-1 on the molybdenum oxide (MoOx) thin layer, forming a 50 nm-thick intrinsic layer (I layer) by co-depositing the compound according to Synthesis Example 1-1 and the compound according to Synthesis Example 2-1 in a ratio of 5:1, and subsequently depositing a 30 nm-thick n-type layer including the compound according to Synthesis Example 2-1. On the active layer, aluminum (Al) is sputtered to form an 80 nm-thick cathode, fabricating an organic photoelectric device.

EXAMPLE 1-2

An organic photoelectric device is fabricated according to the same method as Example 1-1 except for codepositing the compound according to synthesis Example 1-1 and the compound according to Synthesis Example 2-1 in a ratio of 1:1.

EXAMPLE 1-3

An organic photoelectric device is fabricated according to the same method as Example 1-1 except for codepositing the compound according to synthesis Example 1-1 and the compound according to Synthesis Example 2-1 in a ratio of 1:5.

EXAMPLE 2

ITO is sputtered to form an about 100 nm-thick anode on a glass substrate, and a p/n active layer is formed thereon by sequentially depositing a 50 nm-thick p-type layer including the compound according to Synthesis Example 1-1 and a 50 nm-thick n-type layer including the compound according to Synthesis Example 2-1. Aluminum (Al) is sputtered to form an 80 nm-thick cathode, fabricating an organic photoelectric device.

EXAMPLE 3

An organic photoelectric device is fabricated according to the same method as Example 2 except for including a 100 nm-thick n-type layer including the compound according to Synthesis Example 2-2 instead of a 50 nm-thick n-type layer including the compound according to Synthesis Example 2-1.

Comparative Example 1

An organic photoelectric device is fabricated according to the same method as Example 2 except for using the compound according to Synthesis Example 1-4 instead of the compound according to Synthesis Example 1-1 and ZnPc instead of the compound according to Synthesis Example 2-1.

Comparative Example 2

An organic photoelectric device is fabricated according to the same method as Example 2 except for using the compound according to Synthesis Example 1-4 instead of the compound according to Synthesis Example 1-1 and fullerene ($C_{60}$) instead of the compound according to Synthesis Example 2-1.

Comparative Example 3

An organic photoelectric device is fabricated according to the same method as Example 3 except for using the compound according to Comparative Synthesis Example 1 instead of the compound according to Synthesis Example 2-2.

Evaluation 2: Light-Absorption Characteristic of Thin Layer

The organic photoelectric devices according to Examples 1-1 to 3 and Comparative Examples 1 to 3 are compared regarding light-absorption characteristics of the active layers therein depending on a wavelength.

The light-absorption characteristics of the active layers are illustrated referring to FIGS. 11 to 18 and Table 1.

FIGS. 11 to 18 are graphs showing light-absorption characteristics of active layers of the organic photoelectric devices according to Examples 1-1 to 3 and Comparative Examples 1 to 3, respectively.

TABLE 1

| | Full width at half maximum (FWHM) (nm) |
|---|---|
| Example 1-1 | 84 |
| Example 1-2 | 87 |
| Example 1-3 | 87 |
| Example 2 | 84 |
| Example 3 | 87 |
| Comparative Example 1 | 225 |
| Comparative Example 2 | 200 |
| Comparative Example 3 | 163 |

Referring to FIGS. 11 to 15, the active layers in the organic photoelectric devices according to Examples 1-1 to 3 have a maximum absorption peak in a wavelength region of about 500 nm to about 600 nm and may absorb light in a green wavelength region. In addition, referring to FIGS. 11 to 15 and Table 1, the active layers in the organic photoelectric devices according to Examples 1-1 to 3 have a full width at half maximum in a range of about 50 nm to 100 nm, and thus have green wavelength selectivity, and resultantly may increase sensitivity and color purity.

Figure 16:
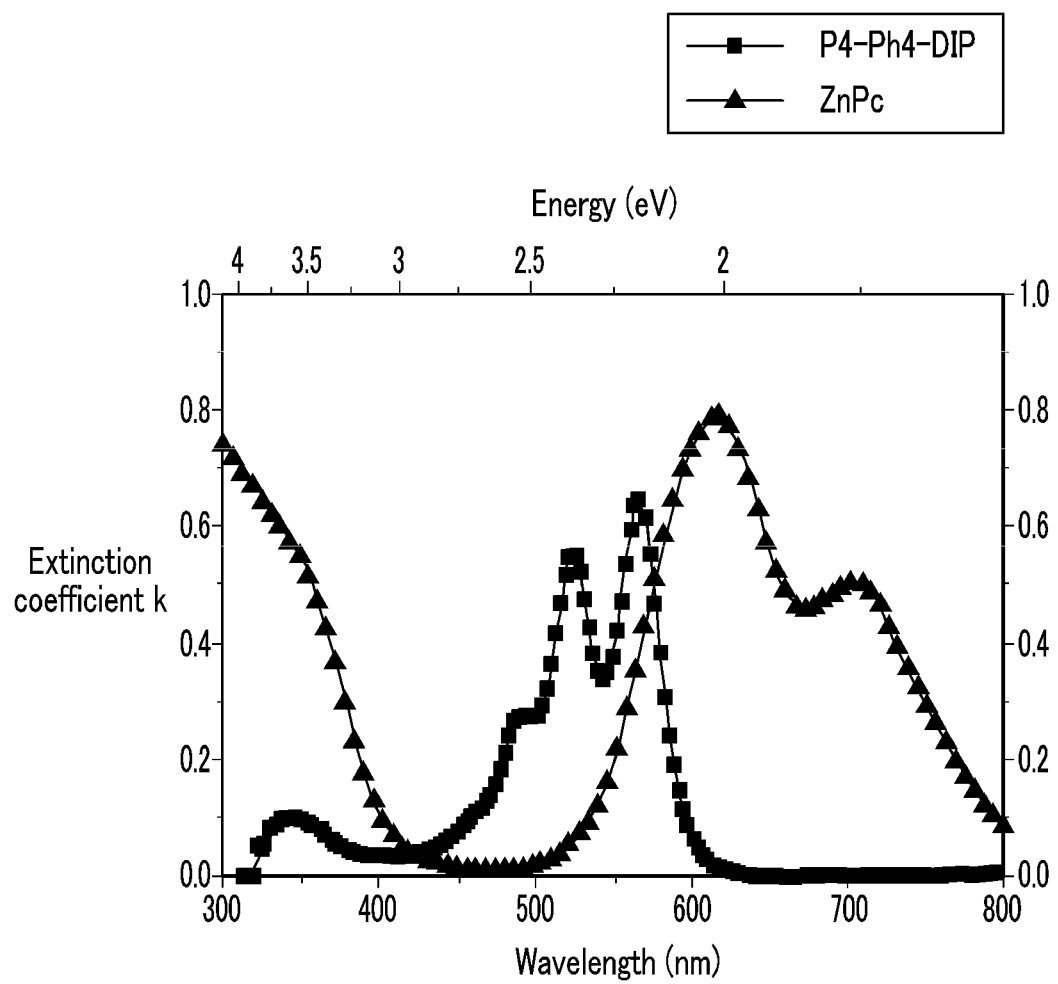
Figure 17:
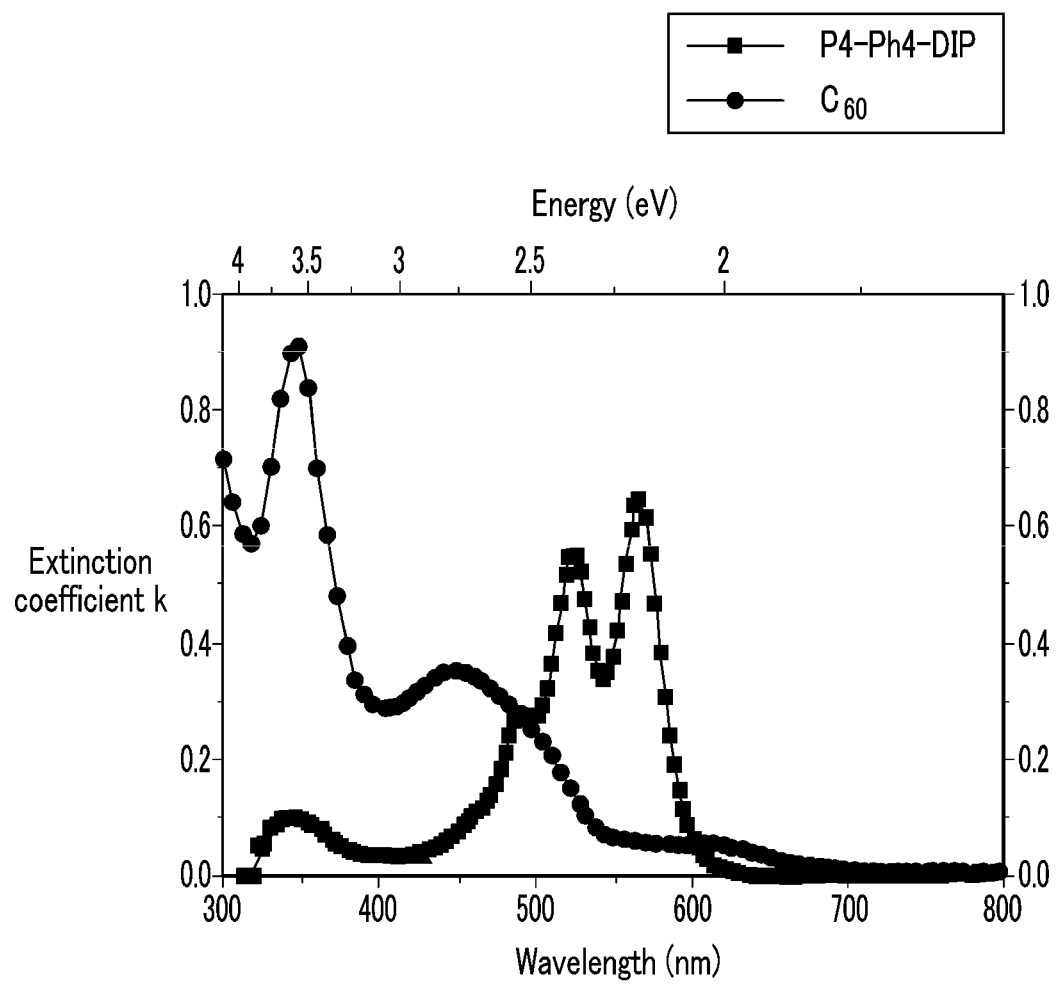
Figure 18:
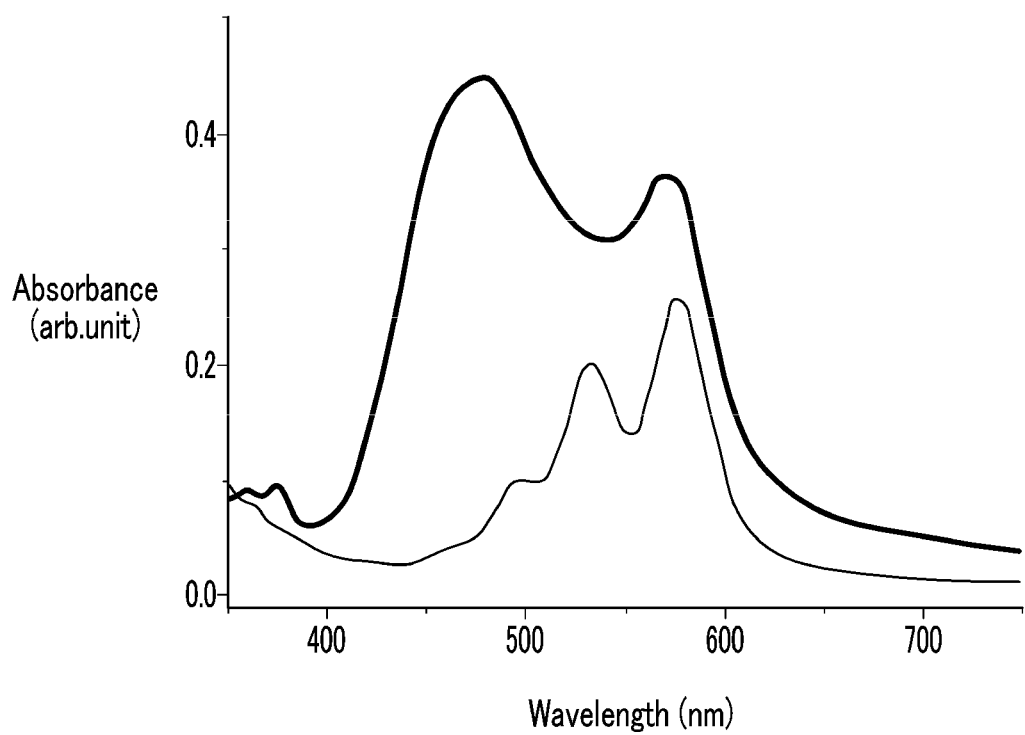

On the contrary, referring to FIGS. 16 to 18, the maximum absorption peak of the active layers in the organic photoelectric devices according to Comparative Examples 1 to 3 is not in a wavelength region of about 500 nm to about 600 nm, and they have a larger full width at half maximum than the active layers in the organic photoelectric devices according to Examples 1-1 to 3.

Evaluation 3

The organic photoelectric devices according to Examples 1-1 to 3 are evaluated regarding external quantum efficiency (EQE) depending on a wavelength.

The external quantum efficiency is measured using an IPCE measurement system (McScience Inc., Korean). First of all, the IPCE measurement system is calibrated using an Si photodiode (Hamamatsu Co., Japan), and then the organic photoelectric devices according to Examples 1-1 to 3 and Comparative Examples 1 to 3 are equipped thereon and measured regarding external quantum efficiency while various biases are applied thereto in a wavelength ranging from about 350 nm to 750 nm.

The results are provided in FIGS. 19 to 23.

Figure 19:
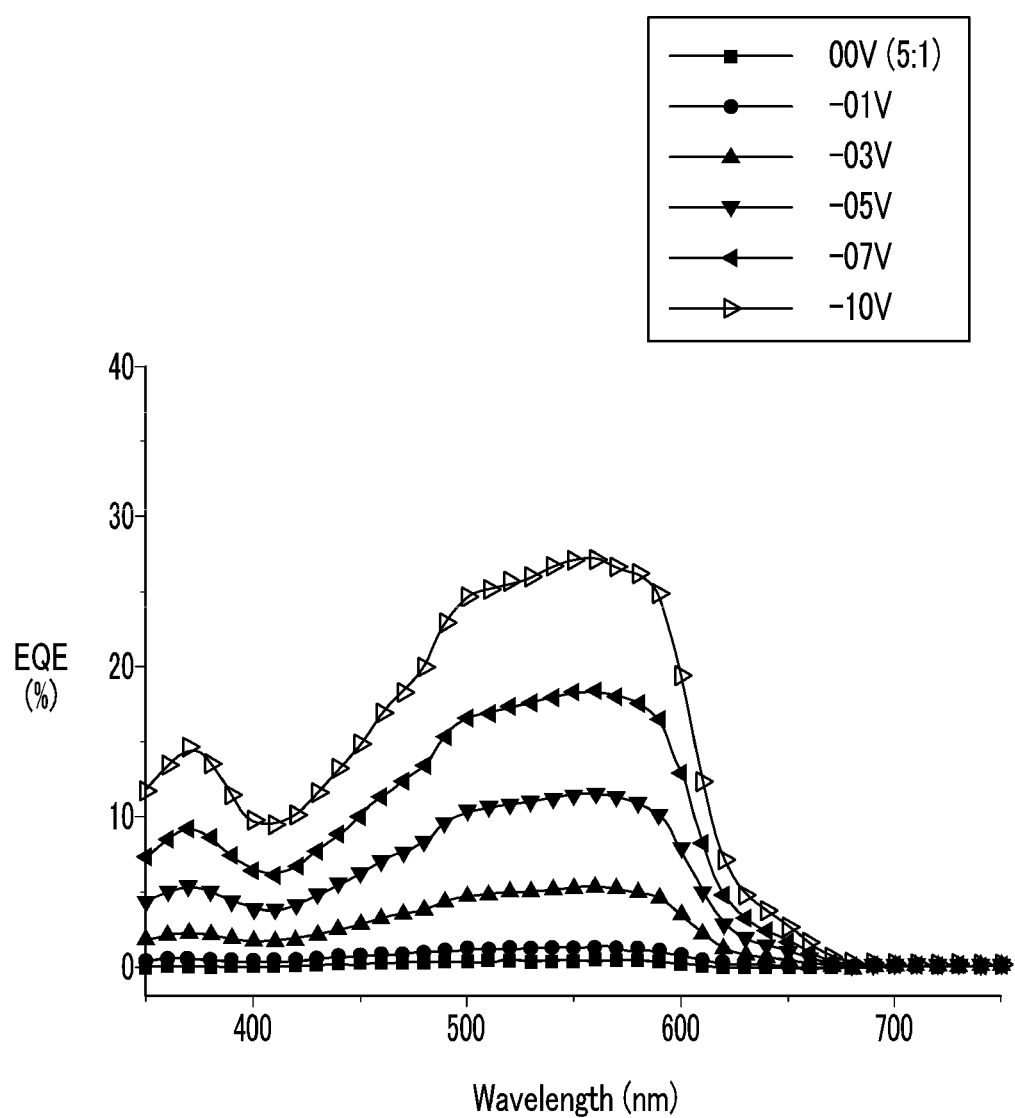
FIG. 19 is a graph showing external quantum efficiency (EQE) of the organic photoelectric device according to Example 1-1 depending on a wavelength and an externally applied voltage.
Figure 20:
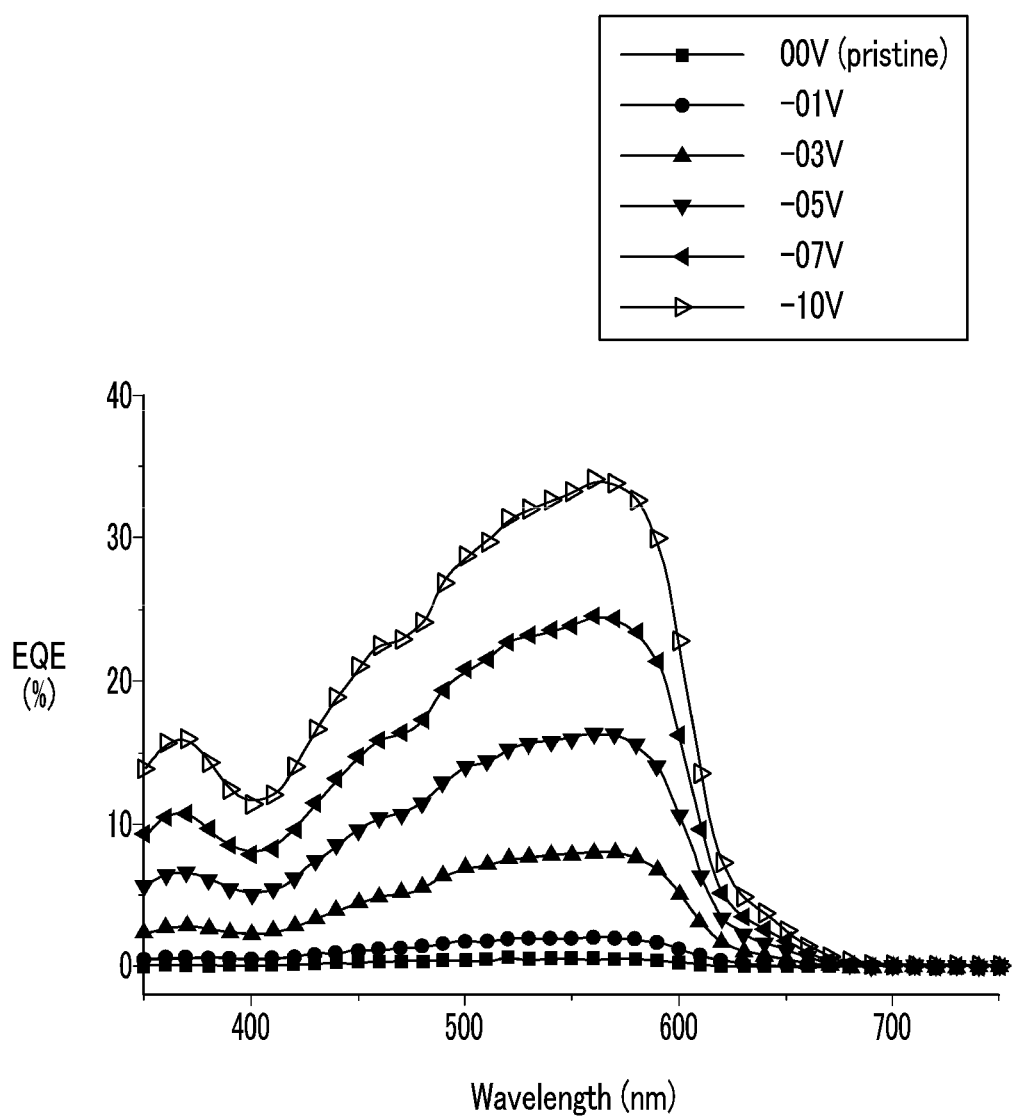
FIG. 20 is a graph showing external quantum efficiency (EQE) of the organic photoelectric device of Example 1-2 depending on a wavelength and an externally applied voltage.
Figure 21:
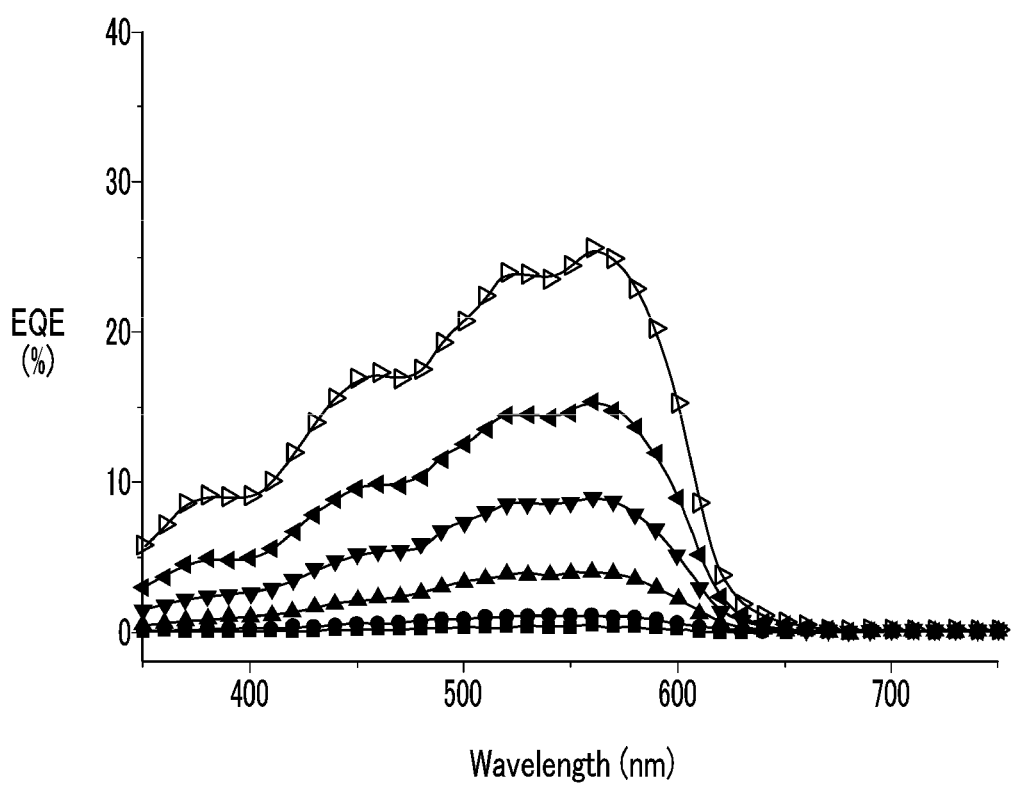
FIG. 21 is a graph showing external quantum efficiency (EQE) of the organic photoelectric device according to Example 1-3 depending on a wavelength and an externally applied voltage.
Figure 22:
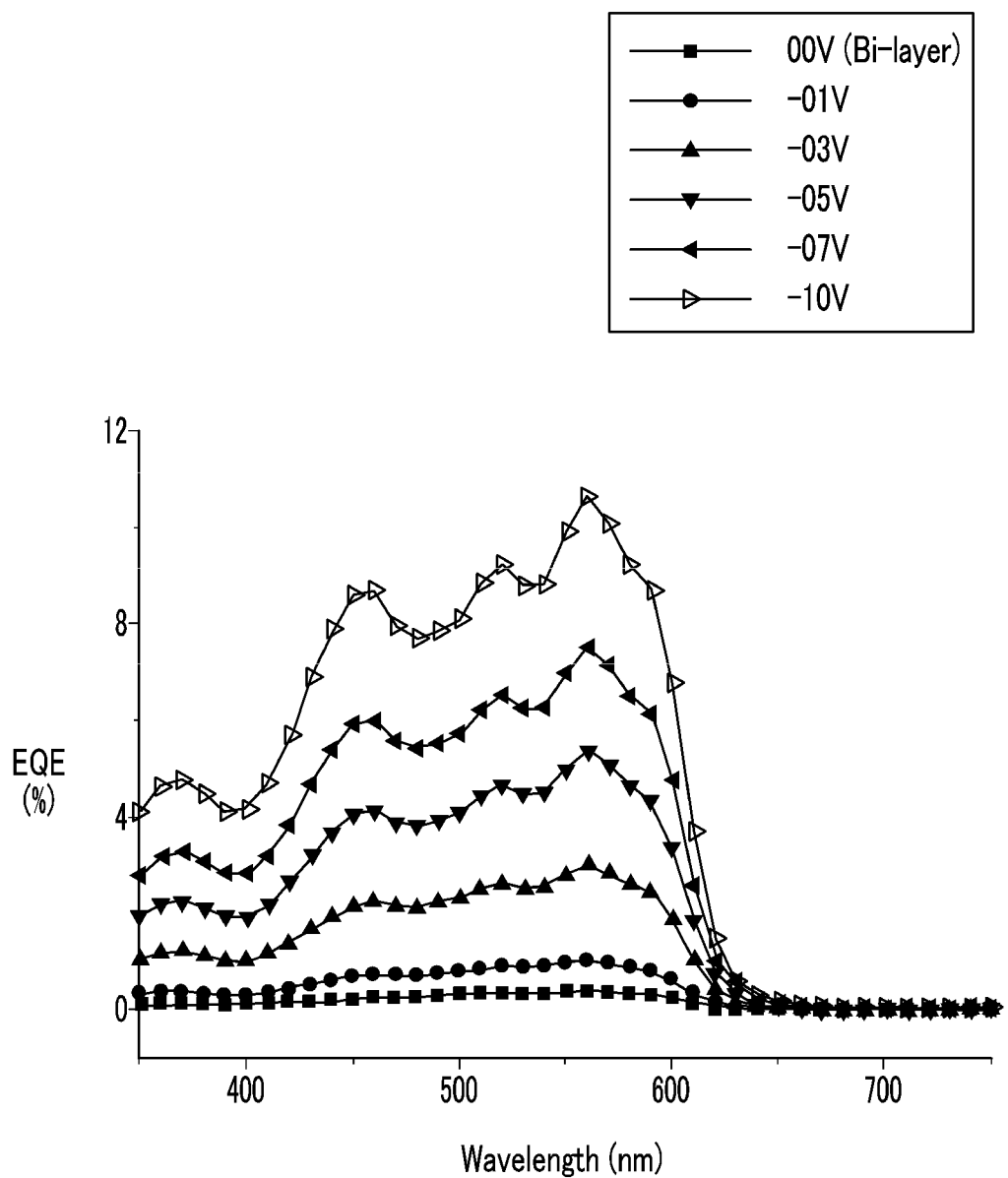
FIG. 22 is a graph showing external quantum efficiency (EQE) of the organic photoelectric device according to Example 2 depending on a wavelength and an externally applied voltage.
Figure 23:
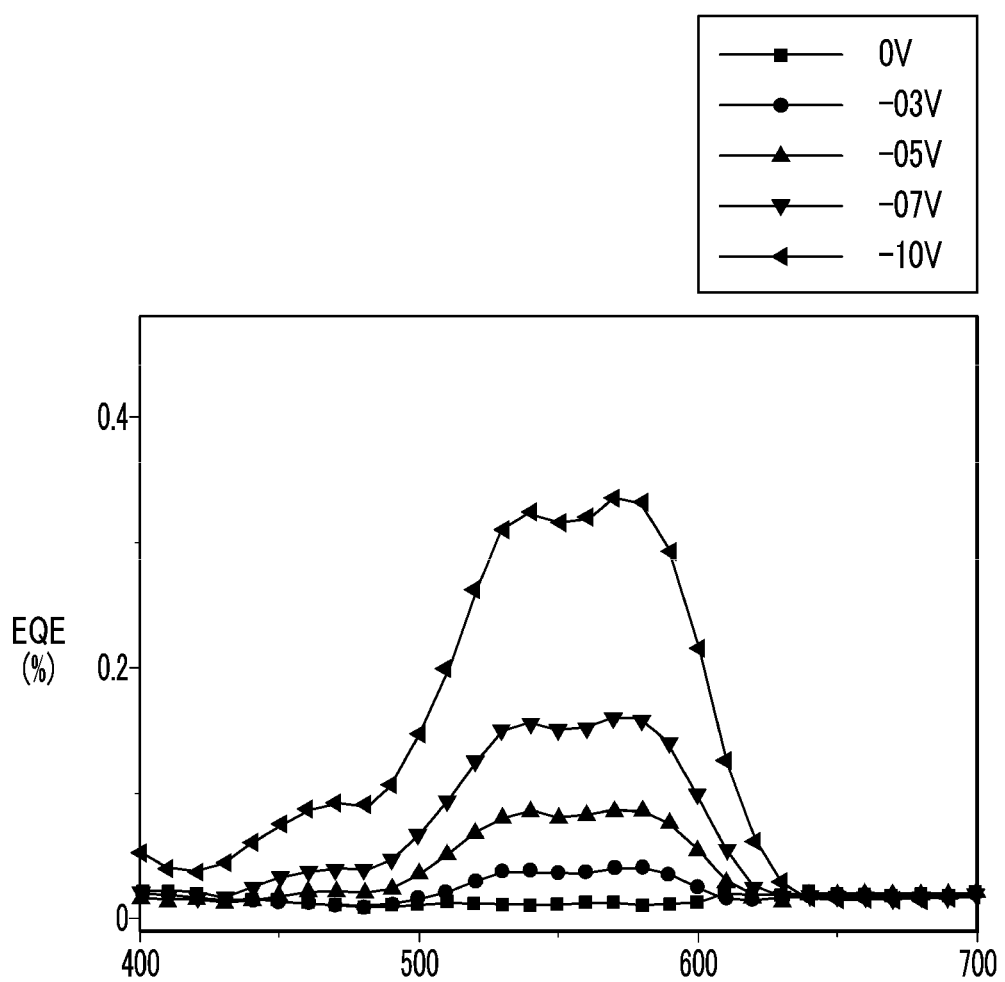
FIG. 23 is a graph showing external quantum efficiency (EQE) of the organic photoelectric device according to Example 3 depending on a wavelength and an externally applied voltage.

FIG. 19 is a graph showing external quantum efficiency (EQE) of the organic photoelectric device according to Example 1-1 depending on a wavelength, FIG. 20 is a graph showing external quantum efficiency (EQE) of the organic photoelectric device of Example 1-2 depending on a wavelength, FIG. 21 is a graph showing external quantum efficiency (EQE) of the organic photoelectric device according to Example 1-3 depending on a wavelength, FIG. 22 is a graph showing external quantum efficiency (EQE) of the organic photoelectric device according to Example 2 depending on a wavelength, and FIG. 23 is a graph showing external quantum efficiency (EQE) of the organic photoelectric device according to Example 3 depending on a wavelength.

Referring to FIGS. 19 to 23, the organic photoelectric devices according to Examples 1-1 to 3 have a maximum external quantum efficiency (EQE) peak in a green wavelength ranging from about 500 nm to 600 nm.

Evaluation 4

The organic photoelectric devices according to Examples 1-1 to 3 are measured regarding current density while light with various strengths is applied thereto.

Figure 24:
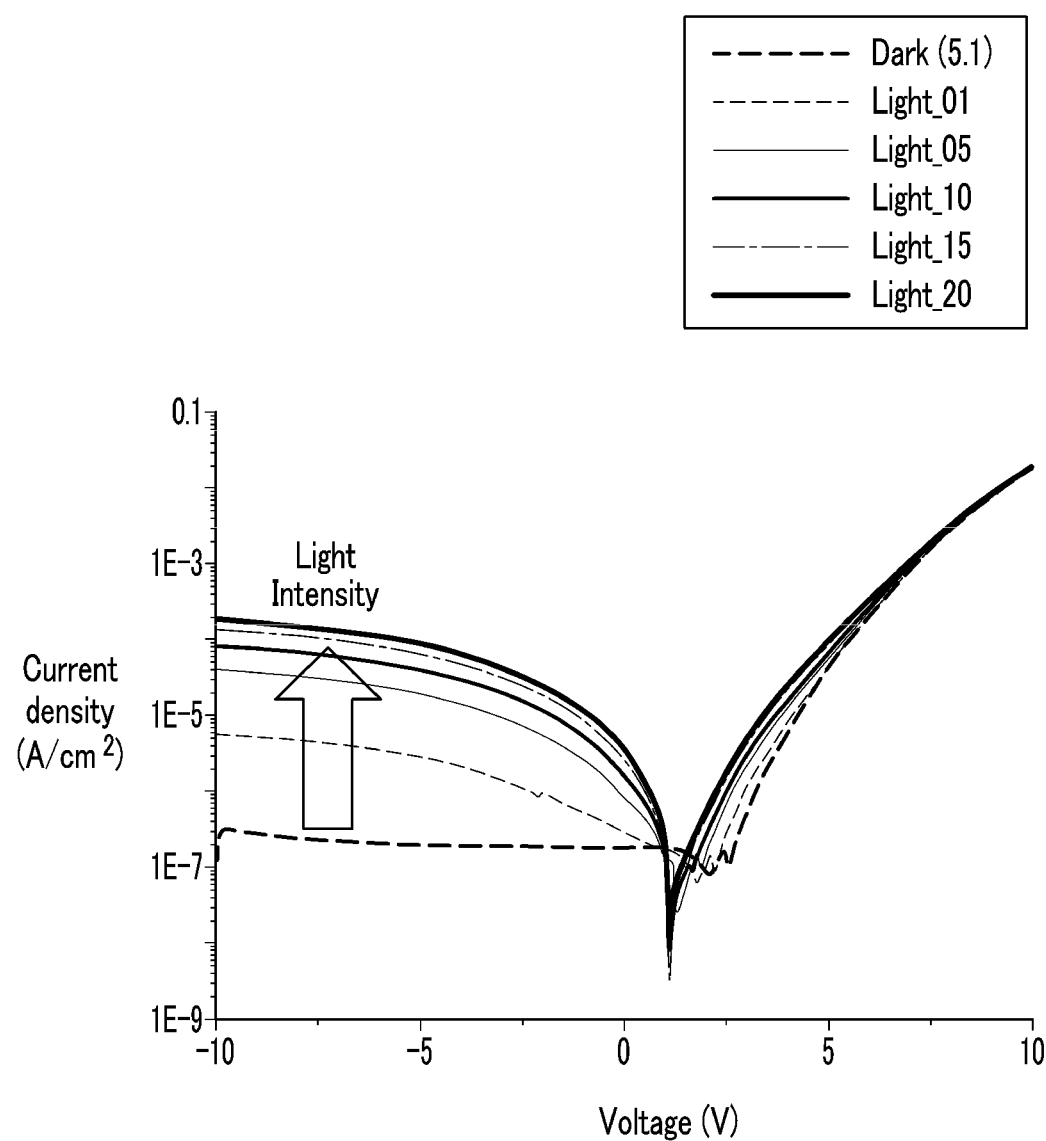
FIG. 24 is a graph showing a current density of the organic photoelectric device according to Example 1-1 depending on intensity of external light.
Figure 25:
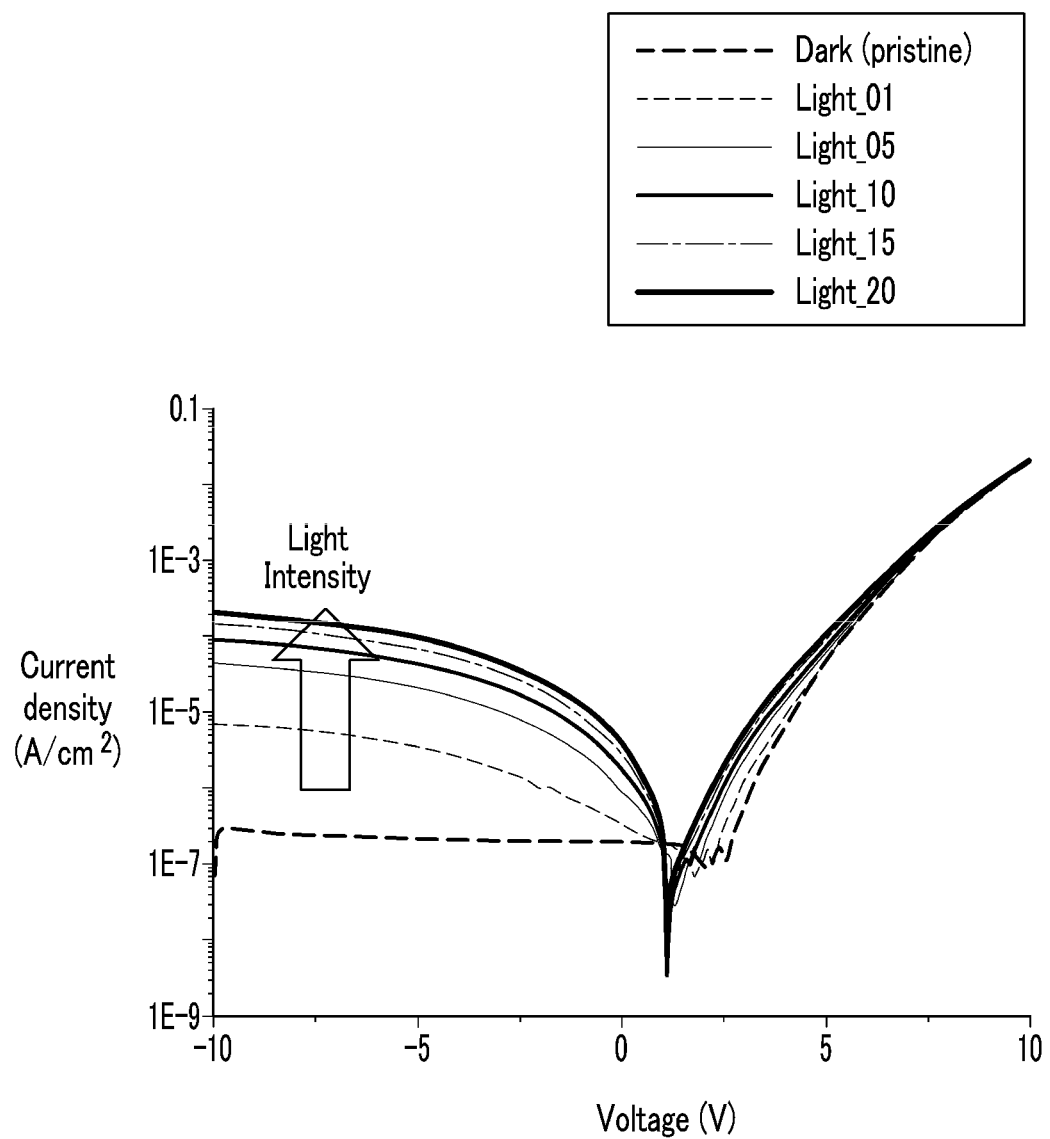
FIG. 25 is a graph showing a current density of the organic photoelectric device according to Example 1-2 depending on intensity of external light.
Figure 26:
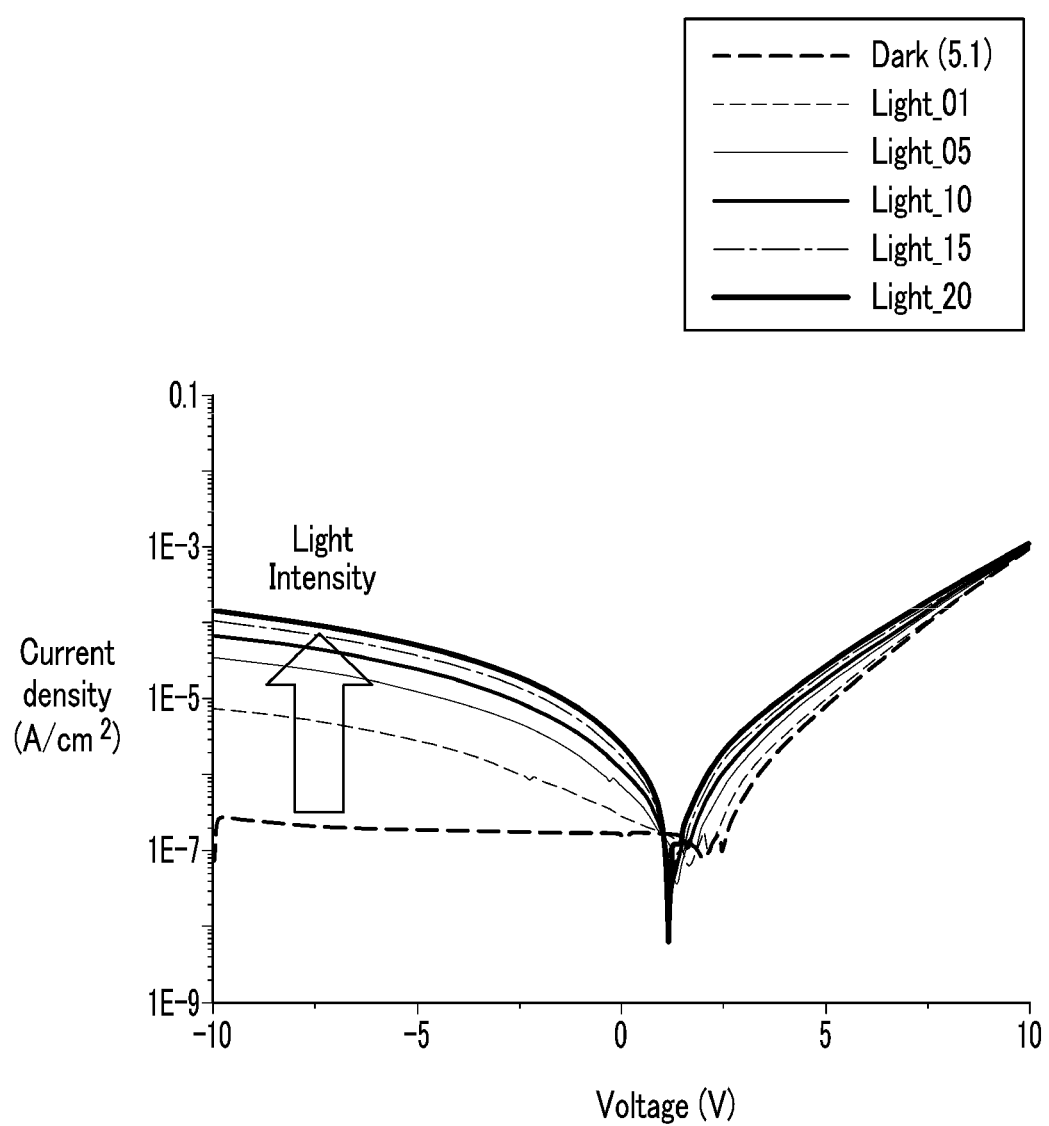
FIG. 26 is a graph showing a current density of the organic photoelectric device according to Example 1-3 depending on intensity of external light.
Figure 27:
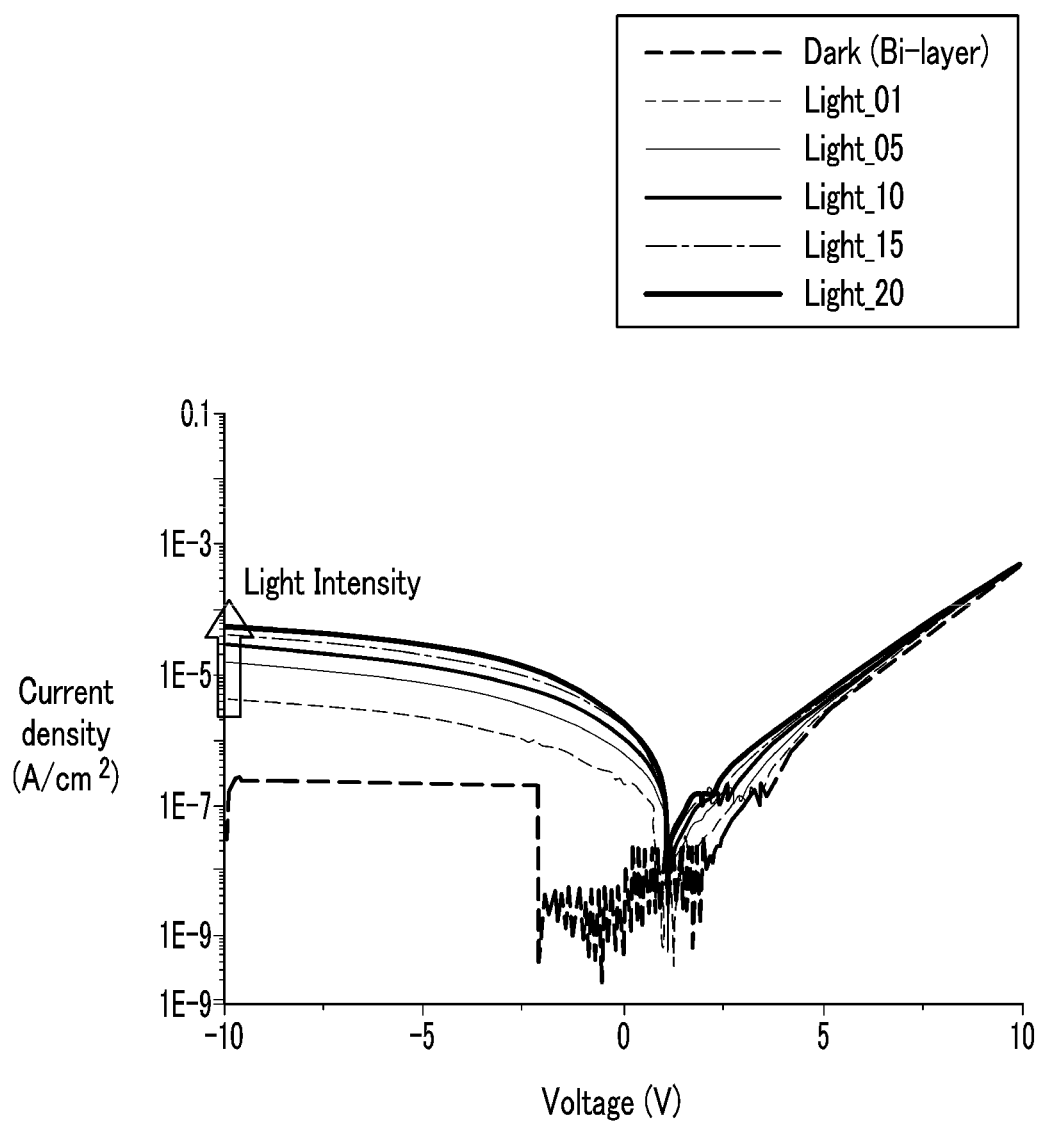
FIG. 27 is a graph showing a current density of the organic photoelectric device according to Example 2 depending on intensity of external light.
Figure 28:
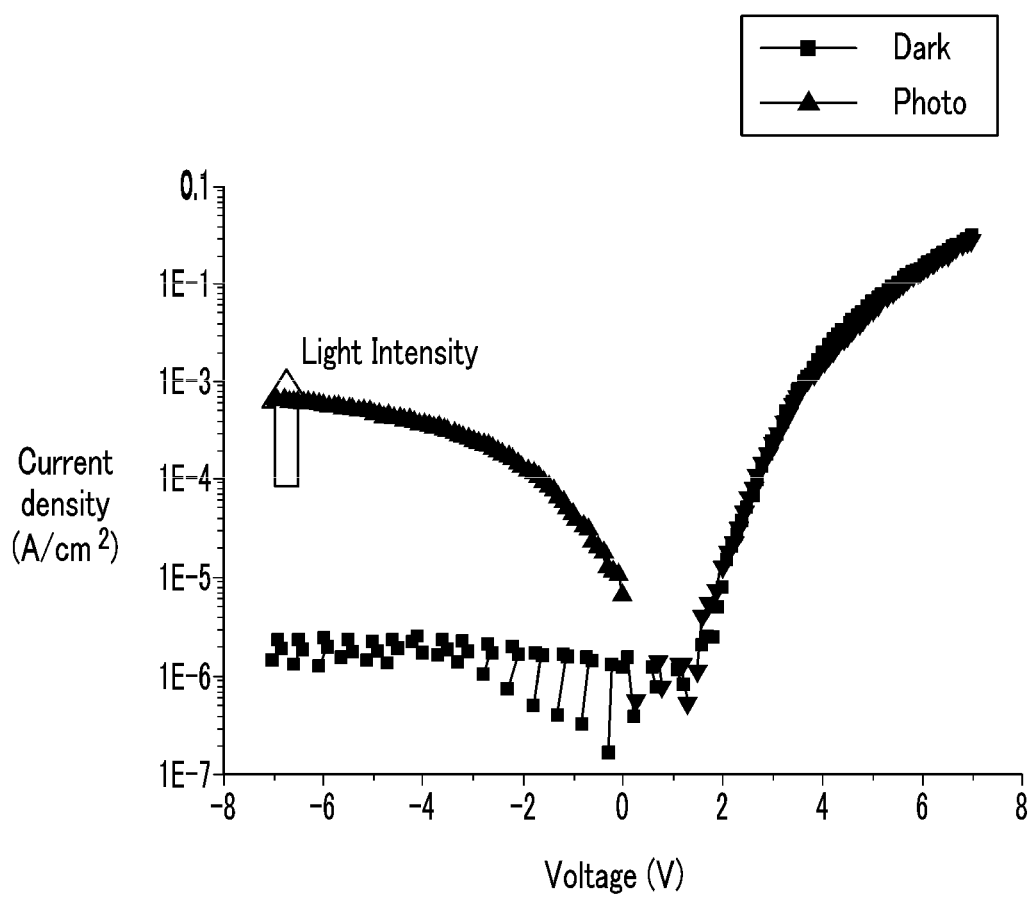
FIG. 28 is a graph showing a current density of the organic photoelectric device according to Example 3 depending on intensity of external light.

FIG. 24 is a graph showing a current density of the organic photoelectric device according to Example 1-1 depending on various intensities of light, FIG. 25 is a graph showing a current density of the organic photoelectric device according to Example 1-2 depending on various intensities of light, FIG. 26 is a graph showing a current density of the organic photoelectric device according to Example 1-3 depending on various intensities of light, FIG. 27 is a graph showing a current density of the organic photoelectric device according to Example 2 depending on various intensities of light, and FIG. 28 is a graph showing a current density of the organic photoelectric device according to Example 2 depending on various intensities of light.

Referring to FIGS. 24 to 28, the organic photoelectric devices according to Examples 1-1 to 3 are suppressed from having current flow in a reverse voltage direction in a dark room having no light. On the contrary, when exposed to light, the organic photoelectric devices have a current flowing in proportion to strength of the light in a reverse voltage direction. Accordingly, strength measurement of the current may be used to quantitatively measure the strength of the externally-entered light.

Evaluation 5

The organic photoelectric device according to Example 1-2 is allowed to stand at 200° C. for 30 minutes and evaluated regarding external quantum efficiency (EQE) characteristic change.

Figure 29:
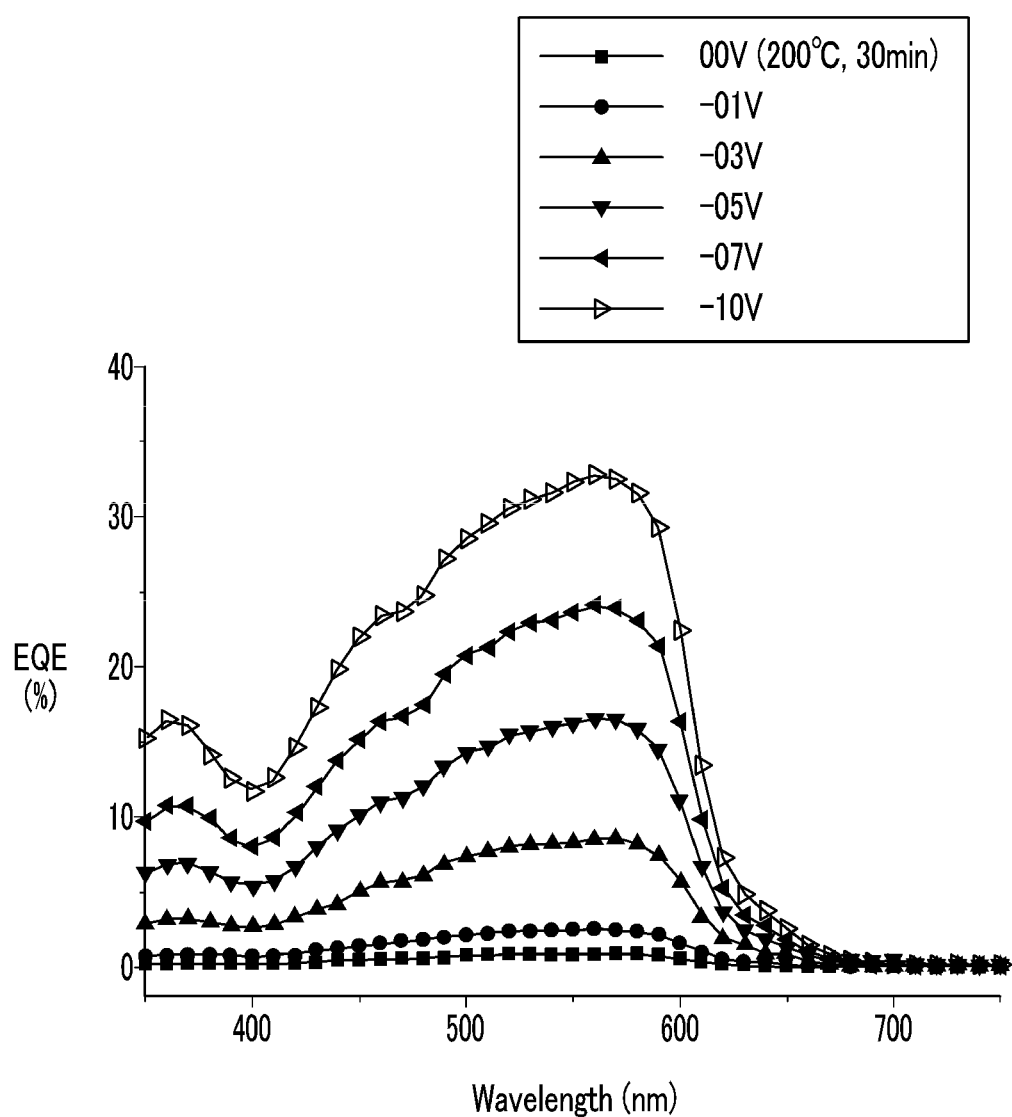
FIG. 29 is a graph showing thermal stability of the organic photoelectric device according to Example 1-2.

FIG. 29 is a graph showing thermal stability of the organic photoelectric device according to Example 1-2.

Referring to FIG. 29, the organic photoelectric device according to Example 1-2 has almost no external quantum efficiency (EQE) characteristic change after being allowed to stand at 200° C. for 30 minutes. Accordingly, the organic photoelectric device according to Example 1-2 has relatively high thermal stability.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An organic photoelectric device, comprising:
   an anode and a cathode facing each other, and
   an active layer interposed between the anode and cathode,
   wherein the active layer comprises a p-type semiconductor compound represented by the following Chemical Formula 1ad and an n-type semiconductor compound represented by the following Chemical Formula 2:

[Chemical Formula 1ad]

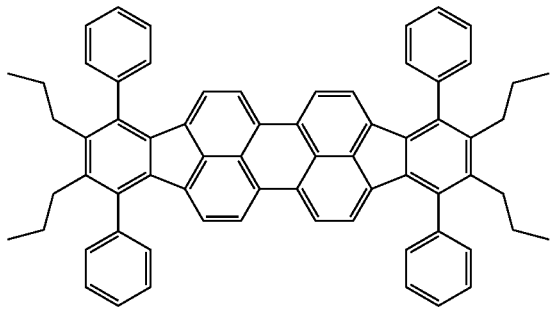

and

[Chemical Formula 2]

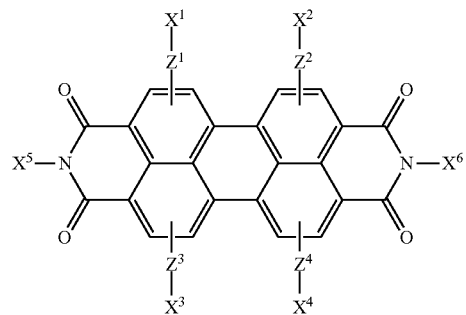

wherein, in Chemical Formula 2,
each of $Z^1$ to $Z^4$ are independently one of oxygen (O), nitrogen (N), and sulfur (S), and each of $X^1$ to $X^6$ are independently one of hydrogen, a substituted or unsubstituted $C_1$ to $C_{30}$ alkyl group, a substituted or unsubstituted $C_3$ to $C_{30}$ aryl group, a substituted or unsubstituted $C_3$ to $C_{30}$ heteroaryl group, and a combination thereof, wherein the p-type semiconductor compound and the n-type semiconductor compound form a pn junction.

2. The organic photoelectric device of claim 1, wherein the compound represented by the above Chemical Formula 2 includes a compound represented by the following Chemical Formula 2a:

[Chemical Formula 2a]

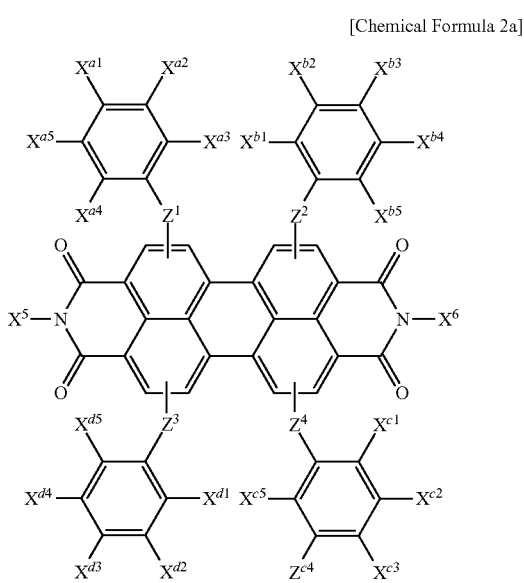

wherein, in Chemical Formula 2a, each of $Z^1$ to $Z^4$ are independently one of oxygen (O), nitrogen (N), and sulfur (S), each of $X^{a1}$ to $X^{a5}$, $X^{b1}$ to $X^{b5}$, $X^{c1}$ to $X^{c5}$, and $X^{d1}$ to $X^{d5}$ are independently one of hydrogen, a substituted or unsubstituted $C_1$ to $C_{30}$ alkyl group, a substituted or unsubstituted $C_6$ to $C_{30}$ aryl group, a halogen atom, a halogen-containing group, and a combination thereof, $X^{a1}$ to $X^{a5}$, $X^{b1}$ to $X^{b5}$, $X^{c1}$ to $X^{c5}$, and $X^{d1}$ to $X^{d5}$ include at least two adjacent groups of $X^{a1}$ to $X^{a5}$, $X^{b1}$ to $X^{b5}$, $X^{c1}$ to $X^{c5}$, and $X^{d1}$ to $X^{d5}$ that are linked to each other to form a ring or fused ring, and each of $X^5$ and $X^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof.

3. The organic photoelectric device of claim 2, wherein the compound represented by the above Chemical Formula 2a includes a compound represented by the following Chemical Formula 2aa, a compound represented by the following Chemical Formula 2ab, or a combination thereof:

[Chemical Formula 2aa]

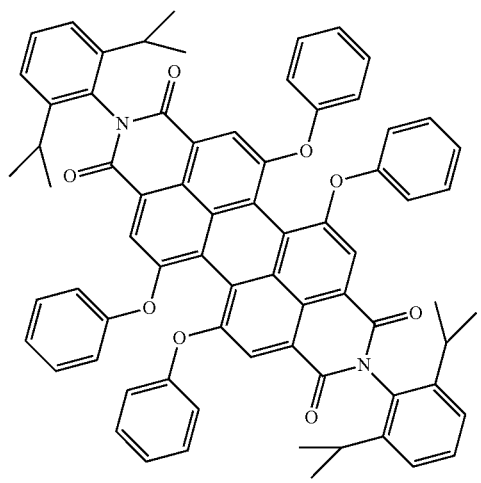

-continued

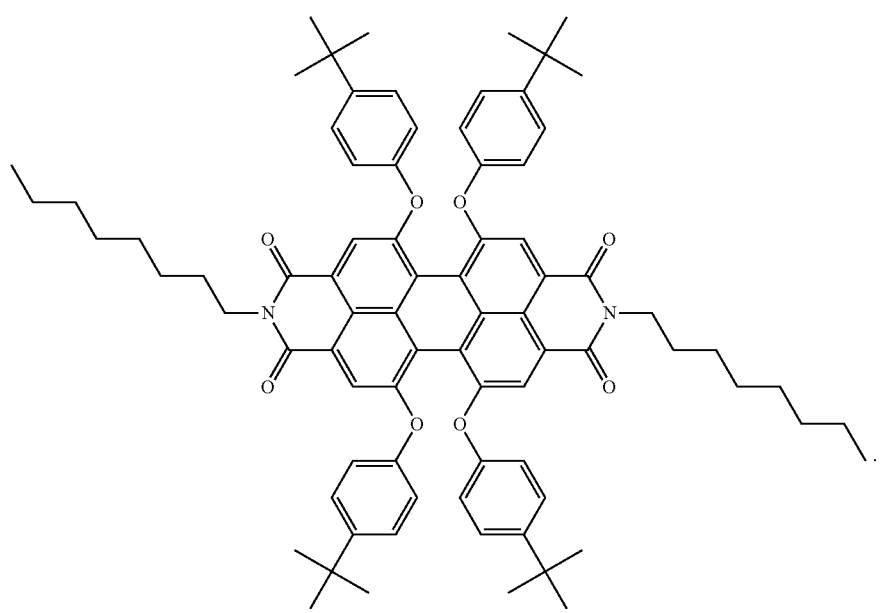

4. The organic photoelectric device of claim 1, wherein the active layer selectively absorbs light in a green wavelength.

5. The organic photoelectric device of claim 1, wherein the active layer has a maximum absorption peak in a wavelength region of about 500 nm to about 600 nm.

6. The organic photoelectric device of claim 1, wherein the active layer has a full width at half maximum (FWHM) of about 50 nm to about 100 nm in a light-absorption curved line.

7. The organic photoelectric device of claim 1, wherein the active layer includes a p-type layer including the compound represented by the above Chemical Formula 1ad and an n-type layer including the compound represented by the above Chemical Formula 2.

8. The organic photoelectric device of claim 1, wherein the active layer includes an intrinsic layer including the compound represented by the above Chemical Formula 1ad and the compound represented by the above Chemical Formula 2 at a ratio of about 1:100 to about 100:1.

9. The organic photoelectric device of claim 8, wherein the active layer includes an intrinsic layer including the compound represented by the above Chemical Formula 1ad and the compound represented by the above Chemical Formula 2 at a ratio of about 1:10 to about 10:1.

10. The organic photoelectric device of claim 8, wherein the active layer further comprises:
a p-type layer including the compound represented by the above Chemical Formula 1ad.

11. The organic photoelectric device of claim 8, wherein the active layer further comprises:
an n-type layer including the compound represented by the above Chemical Formula 2.

12. The organic photoelectric device of claim 11, wherein the active layer further comprises:
a p-type layer on one side of the intrinsic layer and including the compound represented by the above Chemical Formula 1ad; and
an n-type layer on the other side of the intrinsic layer and inchding the compound represented by the above Chemical Formula 2.

13. The organic photoelectric device of claim 1, further comprising:
a charge auxiliary layer between at least one of the anode and the active layer and the cathode and the active layer.

14. An image sensor comprising the organic photoelectric device according to claim 1.

15. An organic photoelectric device, comprising:
an anode and a cathode facing each other, and
an active layer interposed between the anode and cathode,
wherein the active layer comprises a p-type semiconductor compound represented by the following Chemical Formula 1 and an n-type semiconductor compound represented by the following Chemical Formula 2ab:

[Chemical Formula 1]

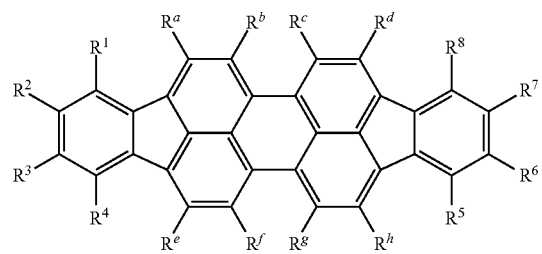

wherein, in Chemical Formula 1,
each of $R^a$ to $R^h$ and $R^1$ to $R^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a halogen atom, a halogen-containing group, and a combination thereof, and $R^a$ to $R^h$ and $R^1$ to $R^8$ include at least two adjacent groups of $R^a$ to $R^h$ and $R^1$ to $R^8$ that are linked to each other to form a ring or fused ring,

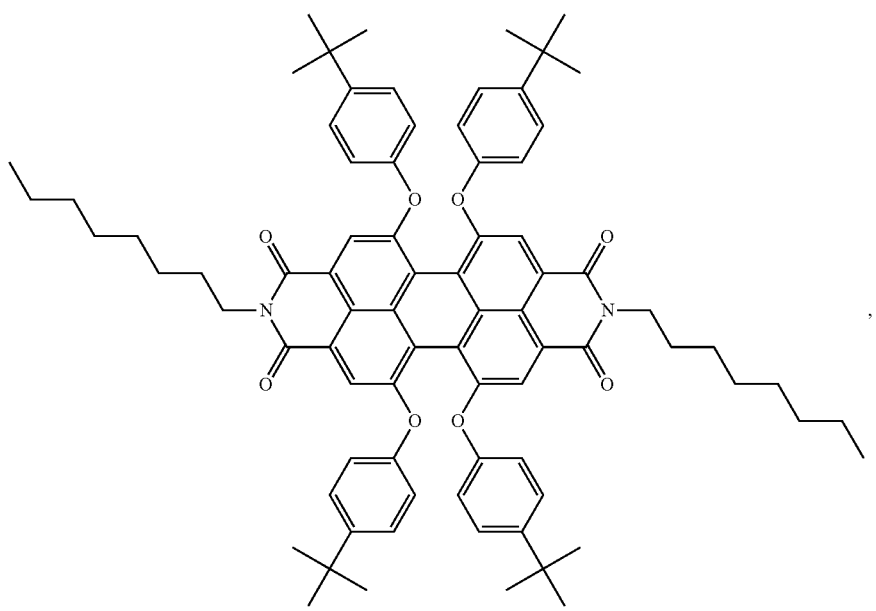

wherein the p-type semiconductor compound and the n-type semiconductor compound form a pn junction.

16. The organic photoelectric device of claim 15, wherein the compound represented by the above Chemical Formula 1 includes a compound represented by the following Chemical Formula 1a:

[Chemical Formula 1a]

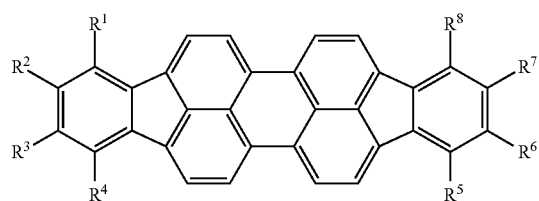

wherein, in Chemical Formula 1a,
each of $R^1$ to $R^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a halogen atom, a halogen-containing group, and a combination thereof,
$R^1$ to $R^8$ include at least two adjacent groups of $R^1$ to $R^8$ that are linked to each other to form a ring or fused ring, and
at least one of $R^1$ to $R^8$ is one of a substituted or unsubstituted $C_6$ to $C_{30}$ aryl group, a substituted or unsubstituted $C_3$ to $C_{30}$ heteroaryl group, and a combination thereof.

17. The organic photoelectric device of claim 16, wherein the compound represented by the above Chemical Formula 1a includes a compound represented by the following Chemical Formula 1aa, a compound represented by the following Chemical Formula 1ab, a compound represented by the following Chemical Formula 1ac, a compound represented by the following Chemical Formula 1ad, or a combination thereof:

[Chemical Formula 2ab]

[Chemical Formula 1aa]

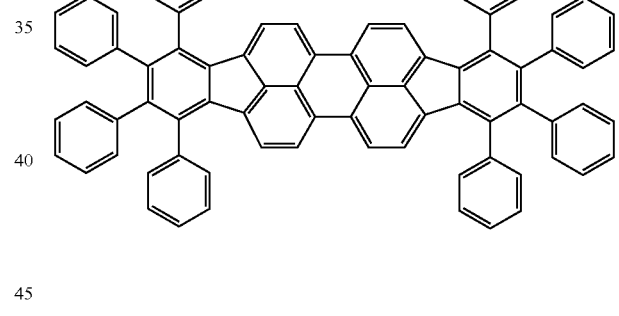

Chemical Formula 1ab]

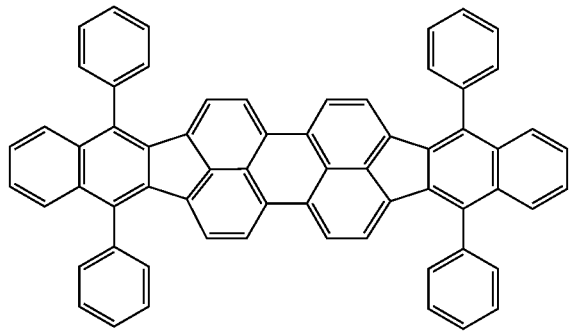

-continued

[Chemical Formula 1ac]

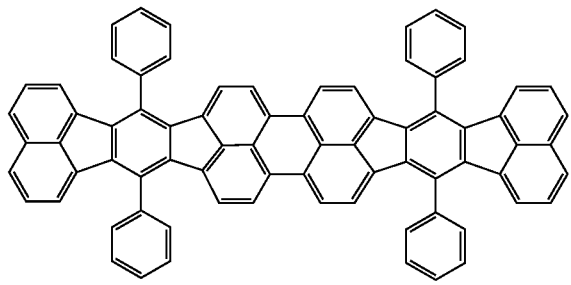

[Chemical Formula 1ad]

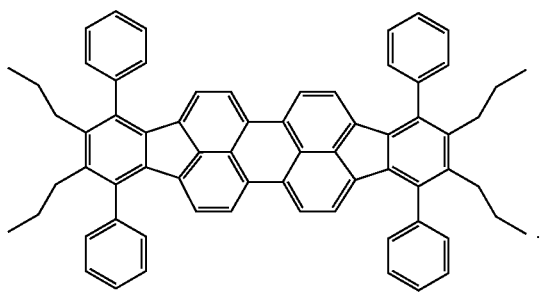

18. The organic photoelectric device of claim 15, wherein the active layer selectively absorbs light in a green wavelength.

19. The organic photoelectric device of claim 15, wherein the active layer has a maximum absorption peak in a wavelength region of about 500 nm to about 600 nm.

20. The organic photoelectric device of claim 15, wherein the active layer has a full width at half maximum (FWHM) of about 50 nm to about 100 nm in a light-absorption curved line.

21. The organic photoelectric device of claim 15, further comprising:

a charge auxiliary layer between at least one of the anode and the active layer and the cathode and the active layer.

22. An image sensor comprising the organic photoelectric device according to claim 15.

* * * * *